US008415463B2

(12) United States Patent
Marillonnet et al.

(10) Patent No.: US 8,415,463 B2
(45) Date of Patent: Apr. 9, 2013

(54) POTEXVIRUS-DERIVED REPLICON

(75) Inventors: Sylvestre Marillonnet, Halle (DE); Carola Engler, Halle (DE); Victor Klimyuk, Halle (DE); Yuri Gleba, Halle (DE)

(73) Assignee: Icon Genetics GmbH, Munich (DE)

( * ) Notice: Subject to any disclaimer, the term of this patent is extended or adjusted under 35 U.S.C. 154(b) by 0 days.

(21) Appl. No.: 12/438,743

(22) PCT Filed: Sep. 6, 2007

(86) PCT No.: PCT/EP2007/007785
§ 371 (c)(1),
(2), (4) Date: Aug. 28, 2009

(87) PCT Pub. No.: WO2008/028661
PCT Pub. Date: Mar. 13, 2008

(65) Prior Publication Data
US 2010/0071084 A1    Mar. 18, 2010

(30) Foreign Application Priority Data

Sep. 6, 2006  (EP) .................................. 06018713

(51) Int. Cl.
*C12N 15/40* (2006.01)
*C12N 15/82* (2006.01)
*C12N 5/10* (2006.01)

(52) U.S. Cl. .................................... 536/23.72; 800/280
(58) Field of Classification Search .................. 800/278
See application file for complete search history.

(56) References Cited

U.S. PATENT DOCUMENTS

2004/0255347 A1* 12/2004 Klimyuk et al. ............. 800/278
2005/0015830 A1*  1/2005 Dorokhov et al. ........... 800/278

FOREIGN PATENT DOCUMENTS

| EP | 1 686 176 A | 8/2006 |
|---|---|---|
| WO | WO 01/38512 A2 | 5/2001 |
| WO | WO 02/088369 A | 11/2002 |

OTHER PUBLICATIONS

Guo et al. Protein tolerance to random amino acid change (2004) PNAS 101: 9205-9210.*
Zayakina et al. (2008) Molec. Plant Path. 9: 37-44.*
Baulcombe, D.C., et al., Jellyfish green fluorescent protein as a reporter for virus infections, *Plant Journal*, 1995, vol. 7(6), pp. 1045-1053.
Chapman, S., et al., "Potato virus X as a vector for gene expression in plants," *The Plant Journal*, 1992, vol. 2(4), pp. 549-557.
Domini, M., et al., "Production of an Engineered Killer Peptide in *Nicotiana benthamiana* by Using a *Potato virus X* Expression System," *Applied and Environmental Microbiology*, 2005, vol. 71(10), pp. 6360-6367.

Fedorkin, O.N., et al., "Cell-to-Cell movement of potato virus X involves distinct functions of the coat protein," *Journal of General Virology*, 2001, vol. 82, pp. 449-458.
Lin, M.K. et al., "Movement of potexvirus requires species-specific interactions among the cognate triple gene block proteins, as revealed by a *trans*-complementation assay based on the bamboo mosaic virus satellite RNA-mediated expression system," *Journal of General Virology*, 2006, vol. 87, pp. 1357-1367.
Lough, T.J., et al., "Cell-to-Cell Movement of Potexviruses: Evidence for a Ribonucleoprotein Complex Involving the Coat Protein and First Triple Gene Block Protein," *Molecular Plant Microbe Interactions*, 2000, vol. 13(9), pp. 962-974.
Marconi, et al., "In planta production of two peptides of the Classical Swine Fever Virus (CSFV) E2 glycoprotein fused to the coat protein of potato virus X," *BMC Biotechnology*, 2006, vol. 6(29), pp. 1-9.
Santi, L., et al., "Protection conferred by recombinant *Yersinia pestis* antigens produced by rapid and highly scalable plant expression system," *P.N.A.S.*, 2006, vol. 103(4), pp. 861-866.
Zhang, et al., "Development of *Bean pod mottle* virus-based vectors for stable protein expression and sequence-specific virus-induced gene silencing in soybean," *Virology*, 2006, vol. 344(2), pp. 401-411.
Beck, D., et al., "Infectious Transcripts and Nucleotide Sequence of Cloned cDNA of the Potexvirus White Clover Mosaic Virus," *Virology*, 1990, vol. 177, pp. 152-158.
Drews, G., et al., *Molekulare Pflanzenvirologie*, 2004, Springer-Verlag Berlin Heidelberg New York, pp. 89-90.
Hammond, J., et al., "Identification and full sequence of an isolate of Alternanthera mosaic potexvirus infecting *Phlox stolonifera*," *Arch Virol*, 2006, vol. 151, pp. 477-493.
Huisman, M., et al., "The Complete Nucleotide Sequence of Potato Virus X and Its Homologies at the Amino Acid Level with Various Plus-stranded RNA Viruses," *J gen. Virol.*, 1988, vol. 69, pp. 1789-1798.
Lin, N., et al., "Nucleotide sequence of the genomic RNA of bamboo mosaic potexvirus," *Journal of General Virology*, 1994, vol. 75, pp. 2513-2518.
Sit, T., et al., "Nucleotide Sequence of Papaya Mosaic Virus RNA," *J gen. Virol.*, 1989, vol. 70, pp. 2325-2331.
Sit, T., et al., "Complete nucleotide sequence of clover yellow mosaic virus RNA," *Journal of General Virology*, 1990, vol. 71, pp. 1913-1920.
Sonoda, S., et al., "Homology-Dependent Virus Resistance in Transgenic Plants with the Coat Protein Gene of Sweet Potato Feathery Mottle Potyvirus: Target Specificity and Transgene Methylation," *Virology*, 1999, vol. 89(5), pp. 385-391.
Xu, H., et al., "The entire nucleotide sequence and genomic organization of potato aucuba mosaic potexvirus," *Arch Virol*, 1994, vol. 135, pp. 461-469.

* cited by examiner

*Primary Examiner* — Russell Kallis
*Assistant Examiner* — Steven Bernacki
(74) *Attorney, Agent, or Firm* — Alston & Bird LLP

(57) ABSTRACT

Nucleic acid comprising or encoding an RNA replica comprising, in this order, the following segments (i) to (iii): i) a nucleic acid sequence encoding a potexvirus RNA-dependent RNA polymerase or a function-conservative variant thereof; ii) a nucleic acid sequence comprising: a) a potexvirus triple gene block or a function-conservative variant thereof and b) a sequence encoding a potexviral coat protein or a function-conservative variant thereof; or a sequence encoding a tobago viral movement protein; and iii) a heterologous nucleic acid sequence expressible from said replica in a plant or in plant tissue.

5 Claims, 9 Drawing Sheets

POTEXVIRUS-DERIVED REPLICON

CROSS REFERENCE TO RELATED APPLICATIONS

This application is the U.S. National Stage of International Application PCT/EP2007/00785 filed Sep. 6, 2007, which designates the U.S. and was published by the International Bureau of English on Mar. 13, 2008, and which claims the benefit of European Patent Application No. 06018713.5 filed Sep. 3, 2006; both of which are hereby incorporated herein in their entirety by reference.

FIELD OF THE INVENTION

The present invention relates to a process of high-yield expression of a gene of interest in a plant, in plant tissue or in plant cells using a potexvirus-derived replicon and to a nucleic acid comprising or encoding a potexviral RNA replicon usable for expressing a gene of interest. The invention further relates to a kit of parts comprising two or more vectors that together encode the RNA replicon of the invention.

BACKGROUND OF THE INVENTION

High-yield expression of heterologous proteins in plants can be achieved using viral vectors. Viral vector systems were predominantly developed for transient expression followed by infection (Donson at al., 1991, *Proc Natl Acad Sci USA*, 88:7204-7208; Chapman, Kavanagh & Baulcombe, 1992, *Plant J.*, 2:549-557) or transfection (Marillonnet et al., 2005, *Nat Biotechnol.*, 23:718-723; Santi et al., 2006, *Proc Natl Acad Sci USA*. 103:861-866; WO2005/049839) of a plant host. The best-established and commercially viable systems are based on plus-sense single-stranded RNA viruses, preferably on Tobacco Mosaic Virus (TMV)-derived vectors (Kumagai at al., 1994, *Proc. Natl. Acad. Sci. USA*, 90, 427-430; Mallory et al., 2002, *Nature Biotechnol.* 20, 622-625; U.S. Pat. No. 5,316,931; U.S. Pat. No. 5,589,367; U.S. Pat. No. 5,866,785; U.S. Pat. No. 5,977,438; WO02088369; WO02097080; WO0229068; U.S. Pat. No. 5,491,076).

Another group of RNA virus-based vectors derived from potexvirus PVX (potato virus X) can also provide for reasonably high yield of recombinant proteins, albeit noticeably lower yield than TMV-derived vectors (Chapman, Kavanagh & Baulcombe, 1992, *Plant J.*, 2:549-557; Baulcombe, Chapman & Santa Cruz, 1995, *Plant J.*, 7:1045-1053; Zhou et al., 2006, *Appl. Microbiol. Biotechnol.*, April 13, epub ahead of print; Zelada at al., 2006, *Tuberculosis*, 86:263-267). Obviously, such system needs further improvement in order to increase the yield of recombinant protein of interest.

In the first generation of systemic viral vectors, a large proportion of plant resources was wasted for the production of viral coat protein that is necessary for systemic movement of a viral replicon. For TMV-derived vectors this problem was solved by removing the coat protein gene and by using agro-infiltration for efficient systemic delivery of replicons, thus significantly boosting the yield of recombinant proteins of interest (WO2005/049839; Marillonnet et al., (2005), *Nat. Biotechnol.*, 23:718-723). However, unlike TMV-derived replicons, potexvirus-derived replicons require viral coat protein not only for systemic, but also for short distance (cell-to-cell) movement. Therefore, the coat protein gene of potexvirus-derived viral vectors cannot be removed without a severe loss of protein expression efficiency. Further, engineering of plant host providing viral coat protein in trans is rarely a good solution because of gene silencing. Also, transgenic plants expressing coat protein might exhibit coat protein-mediated resistance to challenges by plant viruses (Beachy, R N., 1999, *Philos. Trans. R. Soc. Lend B Biol. Sci.*, 354:659-664; Wisniewski et al., 1990, *Plant Cell*, 2:559-567). Another similar phenomenon called heterologous CP-mediated resistance can be a problem, for example when a transgenic plant expressing PVX CP reduces cell-to-cell spread of TMV RNA (Bazzini et al., 2006, *J. Gen. Virol.*, 87:1005-1012). In addition, expression of PVX coat protein in transgenic tobacco plants rescues movement-deficient PVX, but compromises the efficiency of cell-to-cell movement and viral replication (Spillane et al., 1997, *Virology*, 236:76-84). This could be an issue when the use of two viral vectors (e.g. TMV- and PVX-based vectors) in the same plant cell is required for expression of hetero-oligomeric proteins (e.g. for the co-expression of the heavy and light chains of a monoclonal antibody) (WO2006/079546; Giritch et al., 2006, *Proc. Natl. Acad. Sci. USA*, in press).

GENERAL DESCRIPTION OF THE INVENTION

Therefore, it is an object of the invention to provide a potexvirus-based viral vector for high yield expression of a protein of interest in plants, in plant tissue or in plant cells. The viral vector should be capable of cell-to-cell movement and should waste as little resources of a plant host for producing viral coat protein as possible.

This object is solved by a nucleic acid comprising or encoding an RNA replicon comprising, in this order, the following segments:
(i) a nucleic acid sequence encoding an RNA-dependent RNA polymerase or a function-conservative derivative thereof;
(ii) a nucleic acid sequence encoding one or more proteins required for cell-to-cell movement of said replicon in a plant or in plant tissue;
(iii) a heterologous nucleic acid sequence expressible from said replicon in a plant or in plant tissue;
or a complementary sequence thereof.

This object is further solved by a nucleic acid comprising or encoding an RNA replicon comprising, in this order, the following segments:
(i) a nucleic acid sequence encoding an RNA-dependent RNA polymerase or a function-conservative derivative thereof;
(ii) a nucleic acid sequence comprising a potexvirus triple gene block or a function-conservative variant thereof and a potexviral coat protein or a function-conservative variant thereof;
(iii) a heterologous nucleic acid sequence expressible from said replicon in a plant or in plant tissue;
or a complementary sequence thereof.

This object is further solved by a nucleic acid comprising or encoding an RNA replicon comprising, in this order, the following segments:
(i) a nucleic acid sequence encoding an RNA-dependent RNA polymerase or a function-conservative derivative thereof;
(ii) a nucleic acid sequence comprising a potexvirus triple gene block or a function-conservative variant thereof and a tobamoviral movement protein; and
(iii) a heterologous nucleic acid sequence expressible from said replicon in a plant or in plant tissue;
or a complementary sequence thereof.

Said RNA replicon may be a replicon for replicating and expressing said heterologous nucleic acid sequence in a plant or in plant tissue. Said RNA replicon may be built on a potexvirus and uses the replication and expression system of a potexvirus for expressing a heterologous nucleic acid sequence.

The nucleic acid of the invention may be an isolated, or an isolated and purified, nucleic acid. The nucleic acid of the invention is typically used as a vector for transfecting or transforming a plant or plant cells.

The invention further provides a kit of parts comprising at least two vectors (pro-vectors) that are capable of assembling said nucleic acid of the invention in plant cells by site-directed recombination.

The invention also provides a process of expressing a heterologous nucleic acid sequence of interest in a plant or in plant tissue, comprising providing a plant or plant tissue with said nucleic acid of the invention. The invention also provides a process of expressing a heterologous nucleic acid sequence of interest in a plant or in plant tissue, comprising providing a plant or plant tissue with two or more vectors that are capable of assembling said nucleic acid of the invention in plant cells by site-directed recombination.

The inventors have surprisingly identified a way to increase the expression yield of a protein of interest expressed in a plant or in plant tissue from a potexviral vector by a vector design wherein the sequences as defined in item (ii) are positioned after (downstream in 5 to 3' direction) the RNA-dependent RNA polymerase coding sequence (RdRp or RdRP) of item (i) and precede said heterologous nucleic acid sequence of item (iii). In the special case of potexviral vectors, this vector design leads to a cell-to-cell movement capability of the RNA replicon and, at the same time, to higher expression levels of the heterologous nucleic acid compared to conventional potexviral vectors where a heterologous nucleic acid was placed upstream of the potexviral coat protein gene. The effect identified by the inventors may be due to the fact that the position of the sequences of item (ii) leads to lower expression levels of these proteins and to less consumption of plant resources for the expression of these proteins, allowing higher expression levels of the 3' protein of interest. Importantly, the limited expression level of potexviral coat protein in the invention is sufficient for supporting efficient cell-to-cell movement for high-yield expression of the heterologous sequence of interest.

Potexviruses are plant RNA viruses with a plus-sense single-stranded genome. Thus, said nucleic acid of the invention may be RNA being or comprising said RNA replicon or may be DNA encoding said RNA replicon. Herein, the terms "potexviral vector" or "potexviral replicon" mean that the vector or replicon make use of the replication and protein expression system of potexviruses. Said nucleic acid may be built on a natural potexvirus e.g. by using genetic components from a potexvirus. Said nucleic acid of the invention may be obtainable by inserting said heterologous nucleic acid sequence into a nucleic acid construct encoding a potexvirus, whereby said heterologous nucleic acid sequence of interest is inserted downstream of a sequence enocoding the coat protein of said potexvirus. However, various modifications may be made to the various genetic components of a natural potexvirus, such as to the RdRP gene, the triple gene block, the coat protein gene, or to the 5' or 3' non-translated regions of a potexvirus, examples for which are described below.

Said RNA replicon of the invention comprises, in the order from the 5' end to the 3' end, said segments (i) to (iii) of the invention. Further genetic elements will typically be present on said replicon for replication and expression. For being an RNA replicon, i.e. for autonomous replication in a plant cell, said RNA replicon encodes an RdRp or a function-conservative derivative thereof. Said RNA replicon may further have potexviral 5'- or 3'-untranslated regions and promoter-sequences in the 5'- or 3'-untranslated region of said RNA replicon for binding said RdRp and for replicating said RNA replicon. Said RNA replicon further may have sub-genomic promoters in segments of item (ii) and (iii) for generating sub-genomic RNAs for the expression of the proteins encoded by the segments of items (ii) and (iii). If said nucleic acid is DNA, it will typically have a transcription promoter for allowing production by transcription of said RNA replicon in vitro or in planta. An example of a transcription promoter allowing transcription of said RNA replicon from a DNA nucleic acid in planta is the 35S promoter that is widely used in plant biotechnology.

Said segment (i) may encode an RdRp of a potexvirus such as potato virus X, or a function-conservative variant of said potexvirus RdRp. The RdRp used in said RNA replicon may be considered a function-conservative variant of a potexviral RdRp if said sequence of item (i) encodes a protein having a sequence identity of at least 36% to a protein encoded by SEQ ID NO:4. In another embodiment, said sequence identity is at least 45%, in a further embodiment at least 55%, in another embodiment at least 65% and in an even further embodiment at least 75% to a protein encoded by SEQ ID NO:4. These sequence identities may be present over the entire sequence of SEQ ID NO:4. Alternatively, these sequence identities may be present within a protein sequence segment of at least 300 amino acid residues, within a protein sequence segment of at least 500 amino acid residues, within a protein sequence segment of at least 900 amino acid residues, or within a protein sequence segment of at least 1400 amino acid residues.

Herein, amino acid sequence identities may be determined using BLASTX 2.2.14 using the standard settings. The standard settings allow, for example, for sequence gaps in alignments.

In one example, said sequence identity between a protein encoded by SEQ ID NO: 4 and a function-conservative variant of a potexvirus RdRp is 45% in a protein sequence segment of at least 900 amino acid residues. In another example, said sequence identity between a protein encoded by SEQ ID NO: 4 and a function-conservative variant of a potexvirus RdRp is 55% in a protein sequence segment of at least 900 amino acid residues.

Alternatively, the RdRp used in said RNA replicon may be considered a function-conservative variant of a potexviral RdRp if said sequence of item (i) encodes a protein having a sequence homology of at least 50% to a protein encoded by SEQ ID NO:4. In another embodiment, said sequence homology is at least 60%, in a further embodiment at least 70%, and in another embodiment at least 80% to a protein encoded by SEQ ID NO:4. These sequence homologies may be present over the entire sequence of SEQ ID NO:4. Alternatively, these sequence homologies may be present within a protein sequence segment of at least 300 amino acid residues, at least 500 amino acid residues, at least 900 amino acid residues, or at least 1400 amino acid residues. Amino acid sequence homologies may be determined using BLASTX 2.2.14 using the standard settings. The standard settings allow, for example, for sequence gaps in alignments.

In one example, said sequence homology between a protein encoded by SEQ ID NO: 4 and a function-conservative variant of a potexvirus RdRp is 70% in a protein sequence segment of at least 900 amino acid residues. In another example, said sequence identity between a protein encoded by SEQ ID NO: 4 and a function-conservative variant of a potexvirus RdRp is 80% in a protein sequence segment of at least 900 amino acid residues.

Alternatively, the RdRp used in said RNA replicon may be considered a function-conservative variant of a potexviral RdRp if said sequence of item (i) has a sequence identity of at least 55%, of at least 60%, or of at least 70% to SEQ ID NO: 4. Said sequence identities may be present within SEQ ID NO:4, or within a sequence segment of at least 900 nucleotides, within a sequence segment of at least 1500 nucleotides, within a sequence segment of at least 2000 nucleotides, or within a sequence segment of at least 4200 nucleotides of SEQ ID NO:4. Nucleotide sequence identities may be determined using BLASTN 2.2.14 using the standard settings. The standard settings allow, for example, for sequence gaps in the alignments.

Said RNA replicon comprises said nucleic acid sequence of item (ii) for allowing cell-to-cell movement of said RNA replicon in a plant or in plant tissue. Cell-to-cell movement of said RNA replicon is important for achieving expression of the sequence of item (iii) in as many cells of said plant or said tissue as possible. Said nucleic acid sequence of item (ii) may comprise the potexviral triple gene block (abbreviated "TGB" herein) or a function-conservative variant thereof (a review on the TGB is found in *J. Gen. Virol.* (2003) 84, 1351-1366). The potexviral triple gene block encodes three proteins necessary to provide the capability of cell-to-cell movement to a potexvirus. Thus, a variant of said TGB is considered to be a function-conservative variant of the TGB if the variant can provide, optionally with other necessary components, the RNA replicon of the invention with the capability of cell-to-cell movement in a plant or in plant tissue.

An example of a potexviral TGB is the TGB of potato virus X (referred to as "PVX TGB" herein). The PVX TGB consists of three genes encoding three proteins designated 25K, 12K, and 8K according to their approximate molecular weight. The gene sequences encoding the PVX 25K, the PVX 12 K protein, and the PVX 8K protein are given in SEQ ID NO: 9, SEQ ID NO: 11, and SEQ ID NO: 13, respectively. Protein sequences of the PVX 25 K protein, the PVX 12K protein, and the PVX BK protein are given in SEQ ID NO: 10, SEQ ID NO: 12, and SEQ ID NO: 14, respectively.

In one embodiment, said function-conservative variant of a potexvirus TGB is a block of three genes, said block encoding three proteins one of which having a sequence identity of at least 33% to the PVX 25K protein, one having a sequence identity of at least 36% to the PVX 12K protein and one having a sequence identity of at least 30% to the PVX 8K protein. In another embodiment, said function-conservative variant of a potexvirus TGB encodes three proteins one of which having a sequence identity of at least 40% to the PVX 25K protein, one having a sequence identity of at least 40% to the PVX 12K protein, and one having a sequence identity of at least 40% to the PVX 8K protein. In a further embodiment, said function-conservative variant of a potexvirus TGB encodes three proteins one of which having a sequence identity of at least 50% to the PVX 25K protein, one having a sequence identity of at least 50% to the PVX 12K protein and one having a sequence identity of at least 50% to the PVX 8K protein. In a further embodiment, the corresponding sequence identity values are 60% for each protein. In a further embodiment, the corresponding sequence identity values are 70% for each protein.

In another embodiment, said function-conservative variant of a potexvirus TGB encodes three proteins as follows: a first protein comprising a protein sequence segment of at least 200 amino acid residues, said segment having a sequence identity of at least 40% to a sequence segment of the PVX 25K protein; a second protein comprising a protein sequence segment of at least 100 amino acid residues, said sequence segment having a sequence identity of at least 40% to a sequence segment of the PVX 12K protein; and a third protein comprising a protein sequence segment of at least 55 amino acid residues, said sequence segment having a sequence identity of at least 40% to a sequence segment of the PVX 8K protein. In a further embodiment, the corresponding sequence identity values are 50% for each protein. In a further embodiment, the corresponding sequence identity values are 60% for each of said first, second, and third protein.

Said nucleic acid sequence of item (ii) may comprise a further sequence encoding a protein necessary for cell-to-cell movement of said RNA replicon such as a potexviral coat protein or a function-conservative variant thereof. A variant of said potexviral coat protein is considered a function-conservative variant of said coat protein if it is capable of providing said RNA replicon, together with other necessary components such as the TGB, with the capability of cell-to-cell movement in a plant or in plant tissue. In one embodiment where said RNA replicon comprises a potexviral coat protein (or a function-conservative variant thereof), said RNA replicon does not have an origin of viral particle assembly for avoiding spread of said RNA replicon from plant to plant in the form of an assembled plant virus. If said RNA replicon comprises a potexviral coat protein gene (or a function-conservative variant thereof) and a TGB (or a function-conservative variant thereof), it is possible that said TGB is located upstream of said coat protein gene or vice versa. Thus, said potexviral coat protein gene (or a function-conservative variant thereof) and said TGB (or a function-conservative variant thereof) may be present in any order in said nucleic acid sequence of item (ii).

The coding sequence of a PVX coat protein is given as SEQ ID NO: 7, and the amino acid sequence of the PVX coat protein is given as SEQ ID NO: 8. A protein can be considered a function-conservative variant of a potexviral coat protein if it comprises a protein sequence segment of at least 200, alternatively at least 220, further alternatively 237 amino acid residues, said sequence segment having a sequence identity of at least 35% to a sequence segment of SEQ ID NO: 8. In another embodiment, a protein is considered a function-conservative variant of a potexviral coat protein if it comprises a protein sequence segment of at least 200, alternatively at least 220, further alternatively 237 amino acid residues, said sequence segment having a sequence identity of at least 45% to a sequence segment of SEQ ID NO: 8. In alternative embodiments, the corresponding sequence identity values are 55% or 65%.

Alternatively, said nucleic acid sequence of item (ii) may comprise, optionally instead of said sequence encoding said potexviral coat protein, a sequence encoding a plant viral movement protein (MP). An example of a suitable MP is a tobamoviral MP such as an MP of tobacco mosaic virus or an MP of turnip vein clearing virus. Said sequence encoding a plant viral movement protein and said potexvirus TGB (or a function-conservative variant thereof) may be present in any order in said nucleic acid sequence of item (ii).

Said heterologous nucleic acid sequence of item (iii) typically comprises the coding sequence of a protein of interest to be expressed in a plant or in plant tissue. Such coding sequence of item (iii) is also referred to herein as gene of interest. Said sequence of item (iii) is heterologous to said plant virus on which said RNA replicon is based. In many cases, said sequence is also heterologous to said plant or said plant tissue in which it is to be expressed. For being expressible from said RNA replicon in a plant or in plant tissue, said sequence of item (iii) typically comprises a sub-genomic promoter and other sequences required for expression such as ribosome binding site and/or an internal ribosome entry site (IRES). In a preferred embodiment, said heterologous nucleic acid sequence of item (iii) has one gene of interest that codes for one protein of interest.

Said nucleic acid of the invention may comprise a potexvirus 5'-nontranslated region (5'-NTR) and a potexvirus 3'-nontranslated region (3'-NTR).

The process of the invention can be used for producing one protein of interest or more than one protein of interest in a plant or in plant tissue. Said process comprises providing a plant, plant tissue or plant cells with said nucleic acid of the invention. The process of the invention is preferably performed in plants or in plant tissue. In one embodiment, said process is a transient expression process, whereby incorporation of the nucleic acid of the invention into chromosomal DNA of the plant host is not necessary.

If said nucleic acid of the invention is RNA, it may be used for infecting a plant or plant tissue, preferably in combination with mechanical injury of infected plant tissue such as leaves. In another embodiment, said nucleic acid of the invention is DNA and said DNA may be introduced into cells of a plant or plant tissue, e.g. by particle bombardment or by *Agrobacterium*-mediated transformation. *Agrobacterium*-mediated transformation is the method of choice if several plants are to be provided with said nucleic acid of the invention, i.e. for large scale protein production methods.

The process of the invention may be performed using the pro-vector approach (WO02088369; Marillonnet et al., 2004, *Proc. Natl. Acad. Sci. USA*, 101:6852-6857) by providing a plant or plant tissue with said kit or parts of the invention. In cells of said plant, the nucleic acid of the invention is then produced by site-specific recombination between pro-vectors. In one embodiment, a first vector (pro-vector) comprising or encoding segments of items (i) and (ii) and a second vector (pro-vector) comprising or encoding the segment of item (iii) is provided to a plant or plant tissue, wherein said first and said second pro-vector each has a recombination site for allowing assembly of a nucleic acid of the invention by site-specific recombination between said first and said second pro-vector. Two or more vectors may be provided to a plant or to plant tissue by providing mixtures of the vectors or mixtures of *Agrobacterium* strains, each strain containing one of said vectors, to a plant or to plant tissue.

Said one or more than one protein of interest may be purified after production in said plant or plant tissue. Methods or purifying proteins from plants or plant cells are known in the art. In one method, a protein of interest may be directed to a plant apoplast and purified therefrom as described in WO 03/020938.

If one protein of interest has to be produced, a nucleotide sequence coding for said protein of interest may be included in said nucleotide sequence encoding said RNA replicon. If two or more proteins of interest are to be produced in the same plant or in the same plant tissue, said plant or plant cells may be provided with a second nucleic acid comprising or encoding a second or further RNA replicon. Said further RNA replicon may then encode one or more further proteins of interest. In one embodiment, a first and a second nucleic acid of the invention may comprise or encode non-competing RNA replicons as described in WO2006/079546.

The present invention may in principle be applied to any plants for which infectious potexviruses exist and for which viral vector systems were established. In one embodiment, dicotyledonous plants or tissue or cells thereof are used. In another embodiment, *Nicotiana* species like *Nicotiana benthamiana* and *Nicotiana tabacum* are used; preferred plant species other than *Nicotiana* species are *Petunia hybrida*, *Brassica campestris*, *B. juncea*, cress, arugula, mustard, Strawberry spinach, *Chenopodium capitatum*, alfalfa, lettuce, sunflower, potato and cucumber. The most preferred plant RNA viruses the RNA replicons of the invention may be based on are Potexviruses such as potato virus X (PVX), papaya mosaic potexvirus or bamboo mosaic potexvirus.

The major application of the present invention is the production of a protein of interest in plants, plant leaves or plant tissue or cell culture. If the process of the invention is performed in plants, plants that do not enter the human or animal food chain are preferred, like *Nicotiana* species. Plants that do not enter the human or animal food chain can be cultivated in an open field and harvested within a certain period after infection with said RNA replicon. Preferably, whole plants or plant parts shall be confined to a contained environment, e.g. a glasshouse or a designed chamber for the incubation period necessary to provide for desired level of expression.

The efficiency of the production process of the present invention is such that a new dimension in plant expression systems is attained. The expression levels achievable with the present invention are such that expenditures for downstream processing (including separation and purification of the protein of interest) are low enough to make the process of the invention competitive with other large-scale expression systems. The invention provides the first high-yield potexviral plant expression system that can be used on a large scale.

ADVANTAGEOUS EMBODIMENTS OF THE INVENTION

Preferred embodiments as described in dependent claims or as described herein can be combined. For example, the invention provides a nucleic acid comprising or encoding an RNA replicon comprising, in this order, the following segments (i) to (iii):

(i) a nucleic acid sequence encoding a potexvirus RNA-dependent RNA polymerase or a function-conservative variant thereof;

(ii) a nucleic acid sequence comprising:
  (a) a potexvirus triple gene block or a function-conservative variant thereof and
  (b) a sequence encoding a potexviral coat protein or a function-conservative variant thereof; and (iii) a heterologous nucleic acid sequence expressible from said replicon in a plant or in plant tissue;

wherein said function-conservative variant of said potexvirus triple gene block encodes three proteins as follows: a first protein comprising a protein sequence segment of at least 200 amino acid residues, said protein sequence segment having a sequence identity of at least 40% to a sequence segment of SEQ ID NO: 10; a second protein comprising a protein sequence segment of at least 100 amino acid residues, said protein sequence segment having a sequence identity of at least 40% to a sequence segment of SEQ ID NO: 12; and a third protein comprising a protein sequence segment of at least 55 amino acid residues, said protein sequence segment having a sequence identity of at least 40% to a sequence segment of SEQ ID NO: 14;

wherein said function-conservative variant of said potexviral coat protein comprises a protein sequence segment of at least 200 amino acid residues, said sequence segment having a sequence identity of at least 35% to a sequence segment of SEQ ID NO: 8; and wherein said sequence of item (i) encodes a protein having a sequence identity of at least 36% to a protein encoded by SEQ ID NO:4 within a protein sequence segment of at least 300 amino acid residues, preferably at least 500 amino acid residues, more preferably at least 900 amino acid residues, and most preferably at least 1400 amino acid residues.

Sequence identity values given in the above embodiment can be exchanged by more specific identity values and/or larger sequence segments as disclosed in the general description of the invention. Further, the above embodiment can be combined with preferred embodiments as defined in the dependent claims or as described in this description. The above nucleic acid may be used in a process of expressing a heterologous nucleic acid sequence of interest in a plant or in plant tissue such as in Nicotiana plants or Nicotiana plant tissue or cells thereof.

In another embodiment, the invention provides a nucleic acid comprising or encoding an RNA replicon comprising, in this order, the following segments (i) to (iii):
(i) a nucleic acid sequence encoding a potexvirus RNA-dependent RNA polymerase or a function-conservative variant thereof;
(ii) a nucleic acid sequence comprising:
    (a) a function-conservative variant of a potexvirus triple gene block and
    (b) a sequence encoding a function-conservative variant of a potexviral coat protein; and
(iii) a heterologous nucleic acid sequence expressible from said replicon in a plant or in plant tissue;
wherein said function-conservative variants are as defined above.

B depicts T-DNA regions of plasmids pIC22922, pICH22939, pICH22942, pICH22953 and pICH21282. PVX Pol: potato virus X RNA-dependent RNA polymerase; 35S: CaMV 35S promoter; 25K, 12K, 8K: triple gene block; 25K (trunk): truncated gene encoding for 25K protein; CP: PVX coat protein; Pvx ntr: PVX non-translated region; GFP: jellyfish green fluorescent protein; sgc: subgenomic promoter of coat protein gene; int: 5' end of plant intron; AttP and AttB: sequences recognized by site-specific integrase of phage C31.

Figure 3:
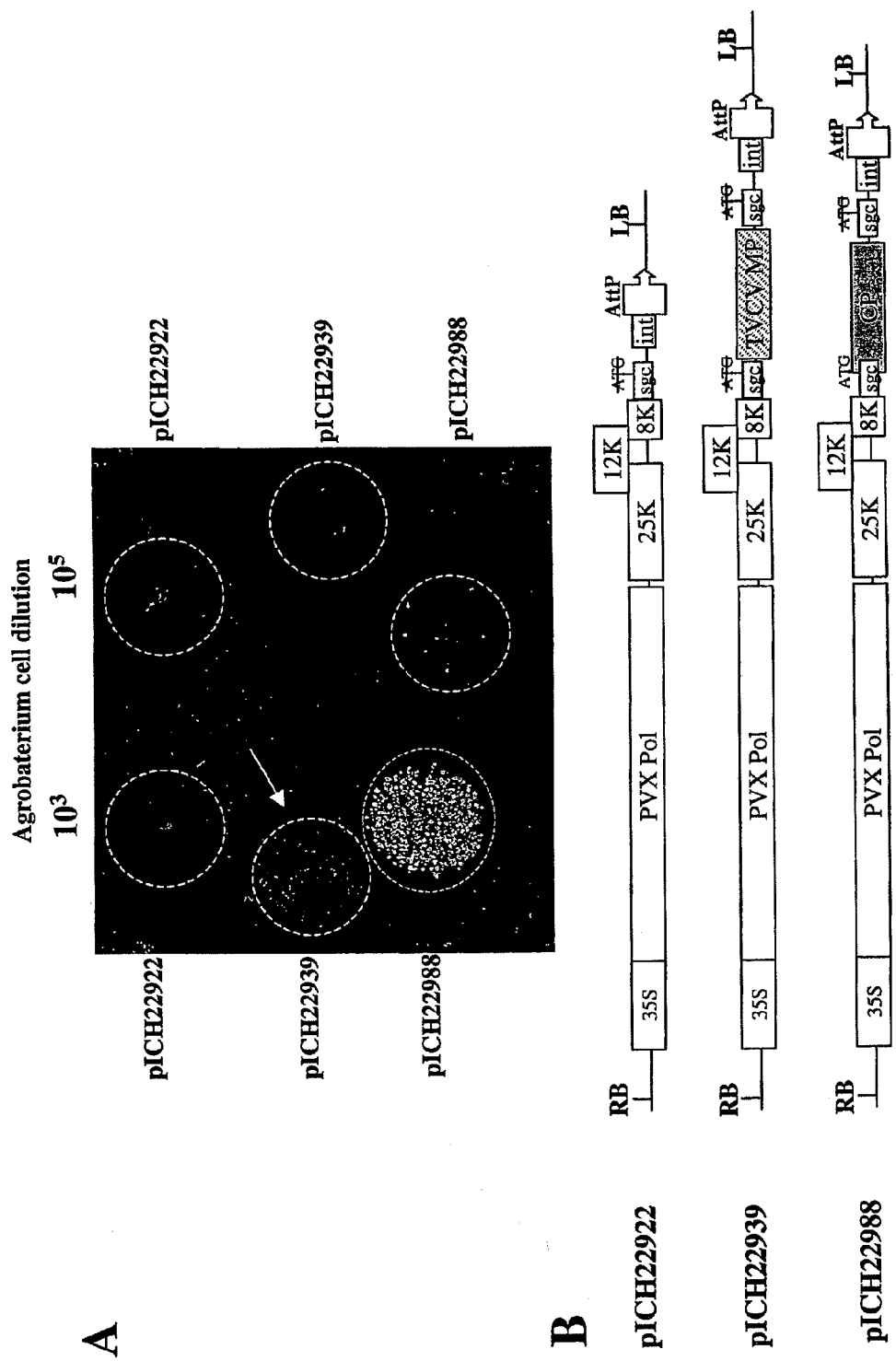

FIG. 3. Comparison of GFP expression using PVX provector modules that do not (pICH22922) or do provide (pICH-122939 or pICH22988) for cell-to-cell movement in plant tissue. A—*N. benthamiana* leaf monitored under UV light after agro-infiltration with different 5' PVX provectors in combination with 3' provector pICH21282 and in the presence of phage C31 integrase providing for site-specific recombination mediated assembly of viral replicon-encoding DNA. The picture was taken 7 days post infiltration (7 dpi). *Agrobacterium* suspensions used for infiltration were diluted $10^3$ or $10^5$ fold as indicated.

B—depicts T-DNA regions of plasmids pIC22922, pICH22939 and pICH22988 pICH22953 and pICH21282. PVX Pol: potato virus X RNA-dependent RNA polymerase; 35S: CaMV 35S promoter; 25K, 12K, 8K: triple gene block; 25K (trunk): truncated gene encoding for 25K protein; TVCV MP: tobamovirus Turnip Vein Clearing Virus movement protein; CP: PVX coat protein; Pvx ntr: PVX non-translated region; GFP: jellyfish green fluorescent protein; sgc: subgenomic promoter of coat protein gene; int: 5' end of plant intron; AttP and AttB: sequences recognized by site-specific integrase of phage C31.

Figure 4:
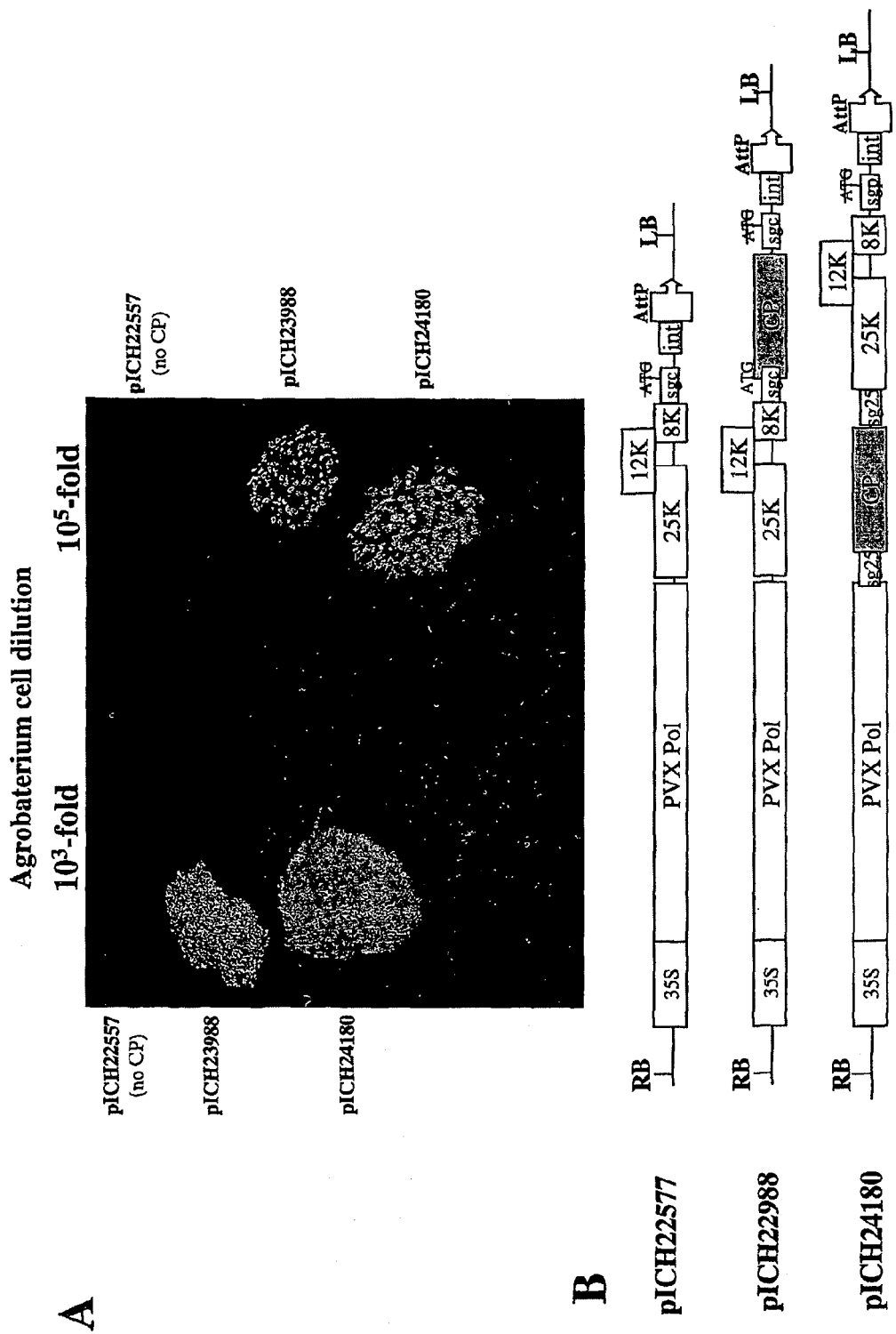

FIG. 4. Comparison of GFP expression using PVX provector modules that do not (pICH22577) or do provide (pICH22988 or pICH24180) for cell-to-cell movement. A—*N. benthamiana* leaf monitored under UV light after agro-infiltration with different 5' PVX provectors in combination with 3' provector pICH21282 and in the presence of phage C31 integrase providing for site-specific recombination-mediated assembly of viral replicon-encoding DNA. The picture was taken 7 days post infiltration (7 dpi). *Agrobacterium* suspensions used for infiltration were diluted $10^3$ and $10^5$ fold as indicated. B—depicts T-DNA regions of plasmids pIC22577, pICH22988 and pICH24180. PVX Pol: potato virus X RNA-dependent RNA polymerase; 35S: CaMV 35Spromoter; 25K, 12K, 8K: triple gene block; CP: PVX coat protein; PVX ntr: PVX non-translated region; sgc: subgenomic promoter of coat protein gene; sg25: subgenomic promoter of 25K gene; int: 5' end of plant intron; AttP: sequence recognized by site-specific integrase of phage C31.

Figure 5:
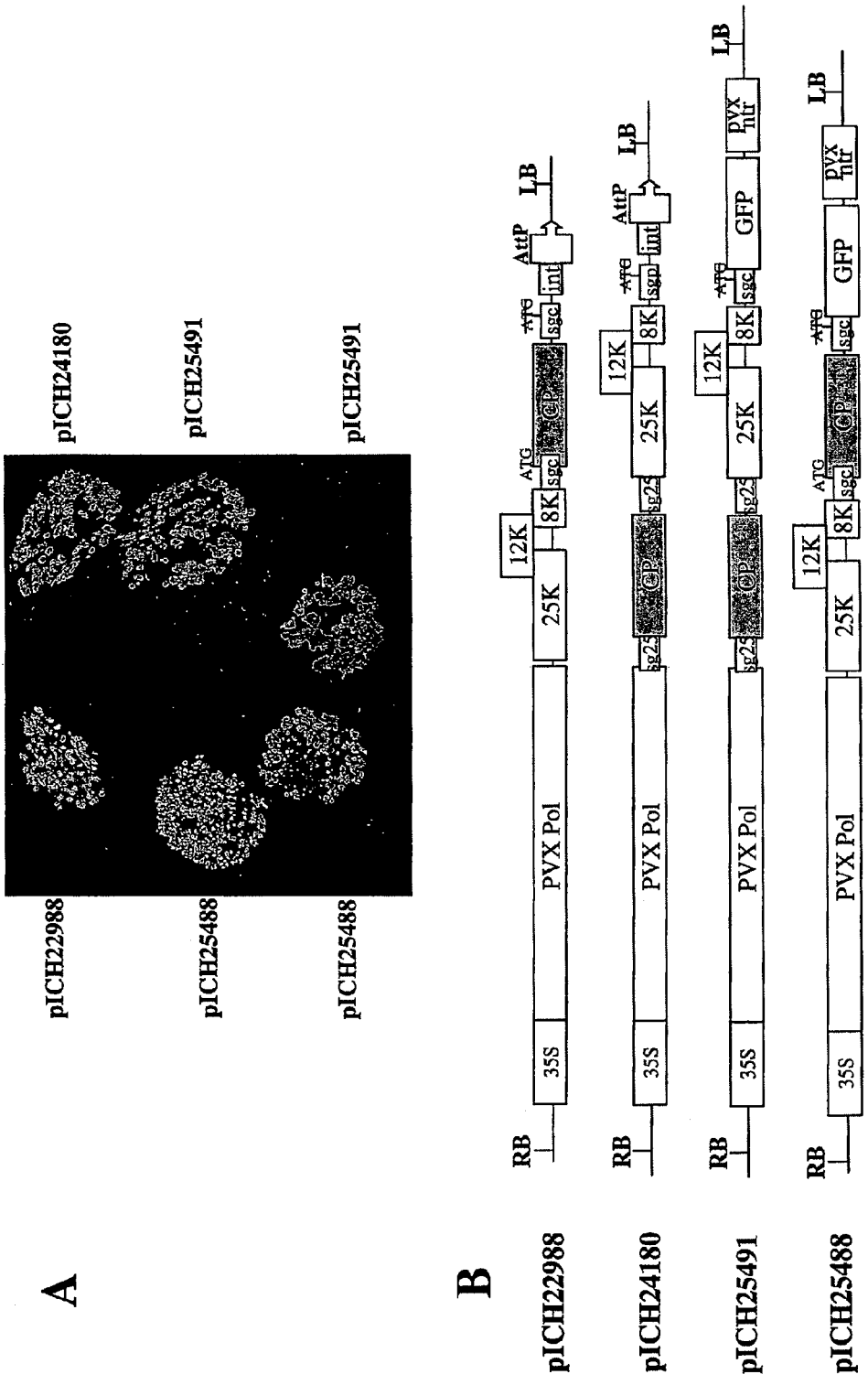

FIG. 5. GFP expression using different PVX expression cassettes (provector modules and assembled vectors) with CP located at different positions in front of the GFP gene. A—*N. benthamiana* leaf monitored under UV light after agro-infiltration with assembled viral vectors pICH25491, pICH25488 or different 5' PVX provectors (pICH22988 or pICH24180) in combination with 3' provector pICH21282 and in the presence of phage C31 integrase providing for site-specific recombination-mediated assembly of viral replicon-encoding DNA. The picture was taken 7 days post infiltration. *Agrobacterium* suspension used for infiltration were diluted $10^5$ fold B—depicts T-DNA regions of plasmids pIC22988, pICH25491, pICH25488 and pICH24180. PVX Pol: potato virus X RNA-dependent RNA polymerase; 35S: CaMV 35Spromoter; 25K, 12K, 8K: triple gene block; CP: PVX coat protein; Pvx ntr: PVX non-translated region; sgc: subgenomic promoter of coat protein gene; sg25: subgenomic promoter of 25K gene; int: 5' end of plant intron; AttP: sequence recognized by site-specific integrase of phage C31.

Figure 6:
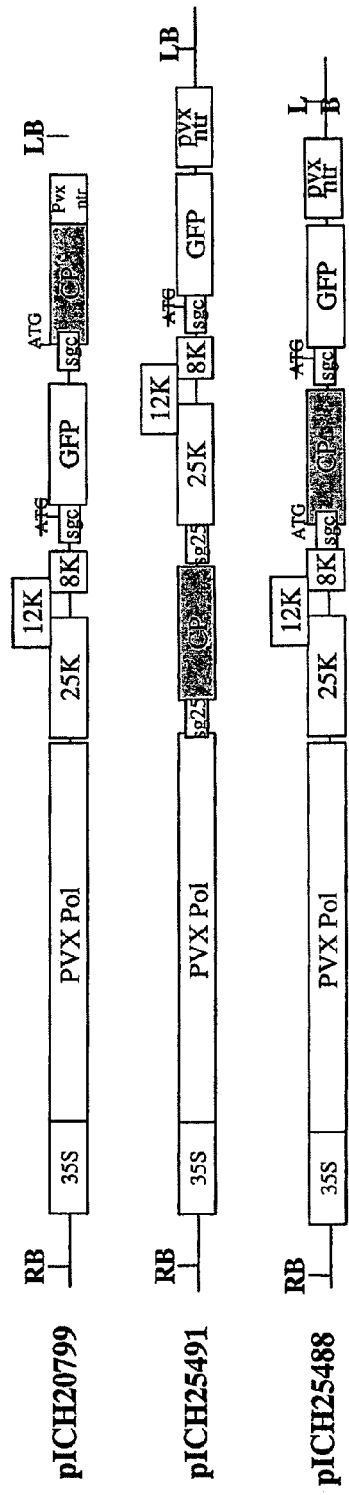

FIG. 6. GFP expression using assembled PVX expression cassettes with CP located at different positions in front of the GFP gene. A—*N. benthamiana* leaves monitored under UV light after agro-infiltration with assembled viral vectors pICH25491, pICH25488 and pICH20799 ten (left panel) and sixteen (right panel) days post-infiltration. *Agrobacterium* suspensions used for infiltration were diluted $10^5$ fold.

B—depicts T-DNA regions of plasmids pIC20799, pICH25491, and pICH25488. PVX Pol: potato virus X RNA-dependent RNA polymerase; 35S: CaMV 35Spromoter; 25K, 12K, 8K: triple gene block; CP: PVX coat protein; PVX ntr: PVX non-translated region; sgc: subgenomic promoter of coat protein gene; sg25: subgenomic promoter of 25K gene.

Figure 7:
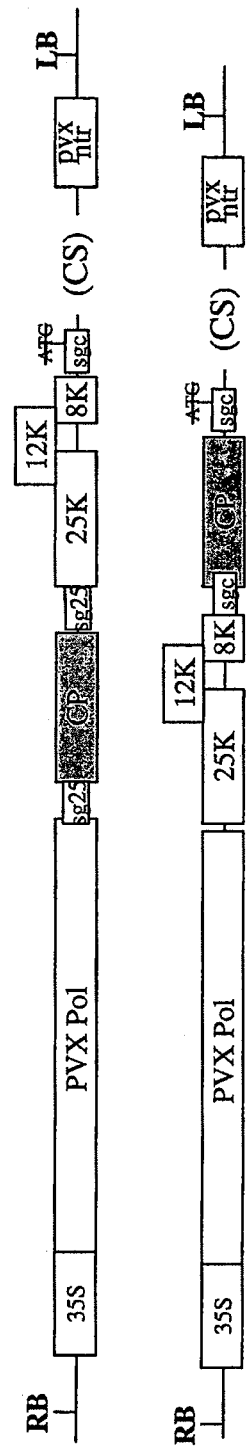

FIG. 7 depicts PVX cloning vectors with multiple cloning sites (CS). PVX Pol: potato virus X RNA-dependent RNA polymerase; 35S: CaMV 35Spromoter; 25K, 12K, 8K: triple gene block; CP: PVX coat protein; PVX ntr: PVX non-translated region; sgc: subgenomic promoter of coat protein gene; sg25: subgenomic promoter of 25K gene.

Figure 8:
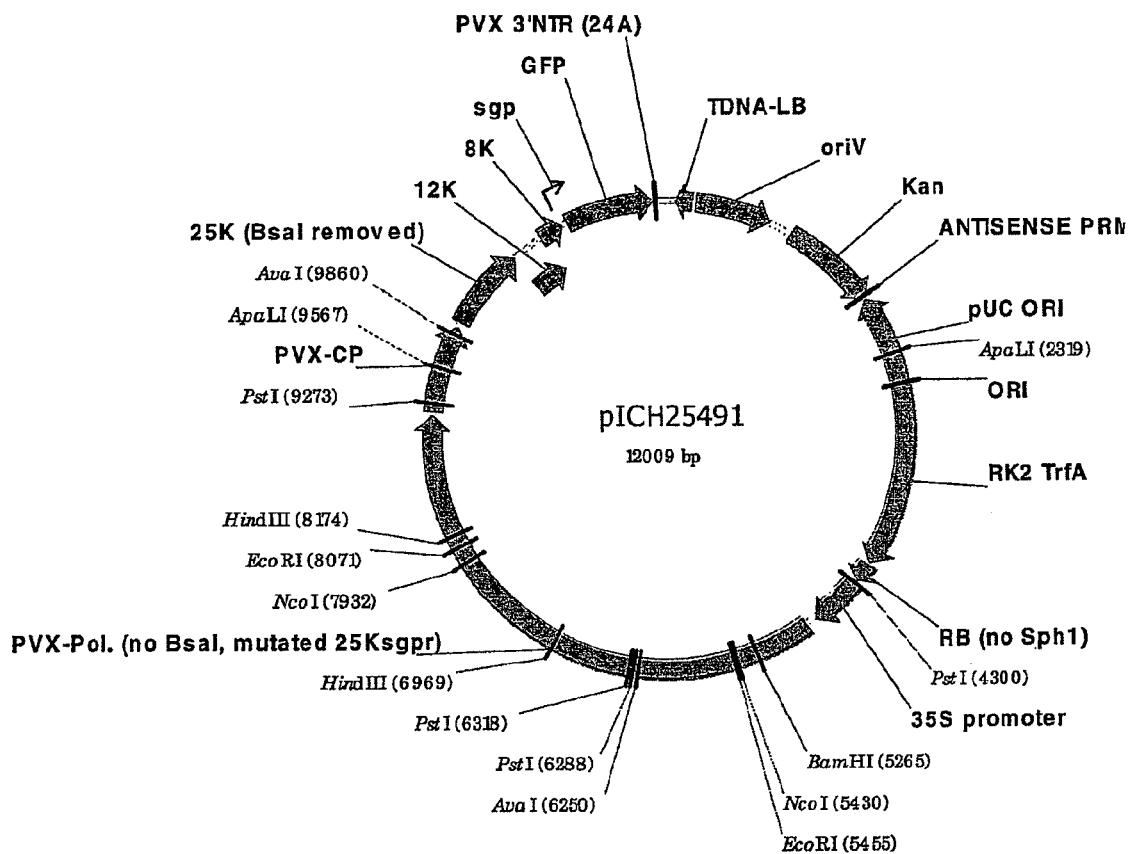

FIG. 8 shows a map of pICH25491. The nucleotide sequence of the T-DNA region of pICH25491 is given in SEQ ID NO:6.

Figure 9:
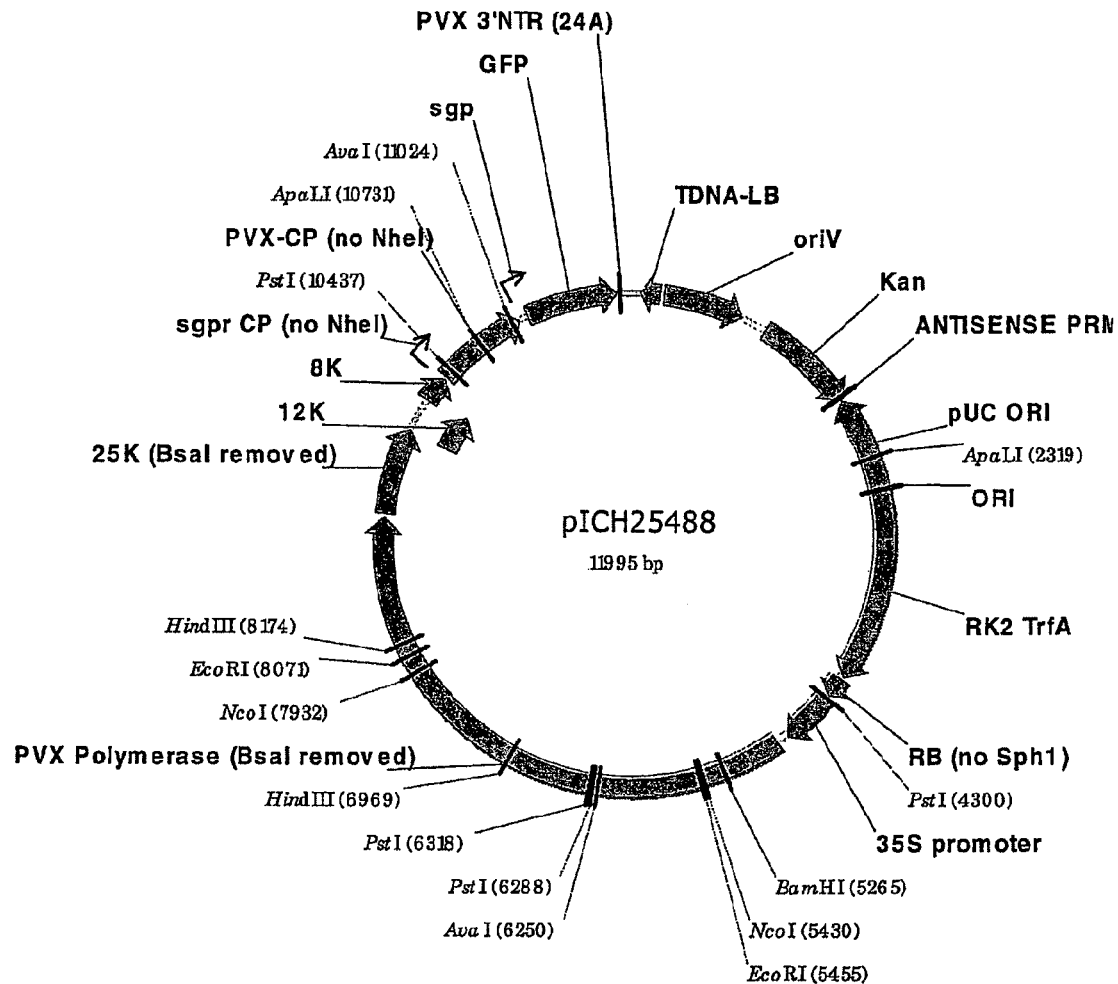

FIG. 9 shows a map of pICH25488. The nucleotide sequence of the T-DNA region of pICH25488 is given in SEQ ID NO:5.

DETAILED DESCRIPTION OF THE INVENTION

This invention describes a new design for potexvirus-derived RNA replicons that improves yield of a protein of interest to be expressed from said RNA replicons in a plant or in plant tissue. The process of the invention has better biosafety features than conventional potexvirus-derived RNA replicons, as it produces less viral coat protein and consequently, can form less viral particles.

Figure 1:
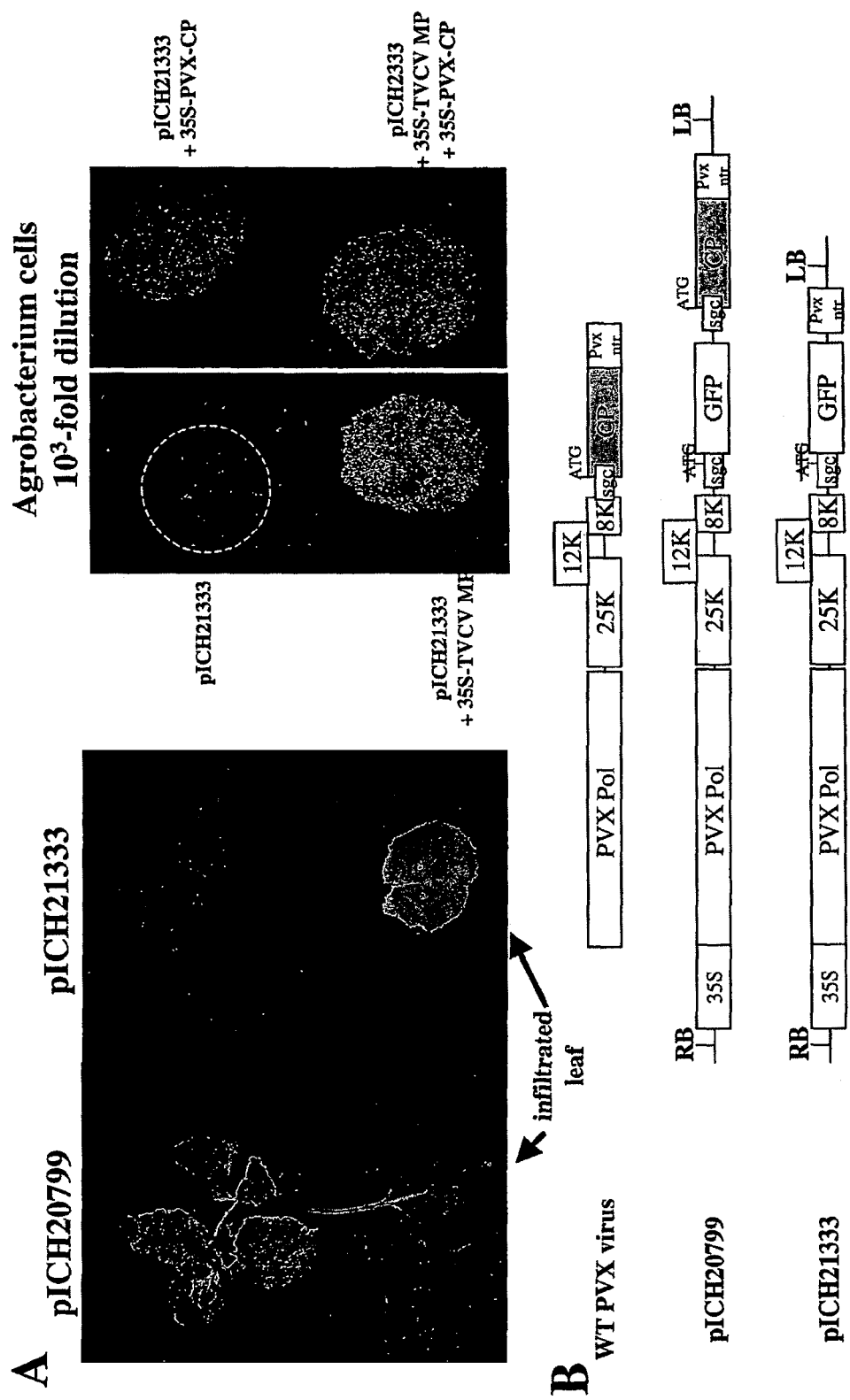
FIG. 1. A—*N. benthamiana* plants (left picture) and plant leaves (right picture) monitored under UV light after agro-infiltration with different PVX vectors. 35S-PVX-CP: vector providing PVX coat protein (CP) under control of CaMV 35S promoter; 35S-TVCV MP: vector providing tobamovirus Turnip Vein Clearing Virus (TVCV) movement protein (MP) under control of CaMV 35S promoter. B—schematic presentation of T-DNA regions of constructs pICH20799 and pICH21333. PVX Pol: potato virus X RNA-dependent RNA polymerase; 35S: CaMV 35S promoter; 25K, 12K, 8K: triple gene block; CP: PVX coat protein; PVX ntr: PVX non-translated region; GFP: jellyfish green fluorescent protein; sgc: subgenomic promoter of coat protein gene; RB: T-DNA right border; LB: T-DNA left border. A crossed-out ATG means that an ATG codon was mutated to prevent translation start at the indicated position.

We have surprisingly found that the position of a coding sequence for a coat protein or heterologous movement protein that precedes said heterologous nucleic acid sequence (iii) encoding a protein of interest increases the yield of said recombinant protein at the expense of viral coat protein. The PVX coat protein is necessary not only for systemic, but also together with three other proteins of triple gene block for cell-to-cell (short distance) movement (Yang et al., 2000, *Mol. Plant Microbe Interact.,* 13:599-605; Fedorkin et al., 2001, *J. Gen. Virol.,* 82:449-458). Herein, it is shown (see example 1 and FIG. 1) that the absence of PVX coat protein makes PVX-derived RNA replicons deficient in long distance (FIG. 1A, left panel) and cell-to-cell (FIG. 1A, right panel) movement. Cell-to cell movement can be restored by providing in trans PVX coat protein (CP) or a tobamoviral movement protein, e.g. tobacco mosaic virus (TMV) movement protein (MP) (FIG. 1A, right panel). It is also shown (example 2, FIG. 2) that a PVX-derived RNA replicon with a TVCV movement protein is capable of short distance (cell-to-cell) movement. The experiment was carried out using the provector system (Marillonnet et al., 2004, *Proc. Natl. Acad. Sci. USA,* 101:6852-6857) that allows assembly in planta of a DNA precursor of an RNA replicon via site-specific recombination e.g. between AttP and AttB sites of provectors (FIG. 2B).

A comparative analysis of PVX-derived RNA replicons with either TVCV MP (pICH22939) or PVX CP is described in example 3 and shown in FIG. 3. As in the case described above, the provector system was used. It is evident from FIG. 3 that PVX CP positioned in front of the gene of interest provides for cell-to-cell movement of said RNA replicon. As it follows from the brightness and density of GFP spots (FIG. 3A), the efficiency of cell-to-cell movement is significantly higher than with TVCV MP.

In another embodiment of this invention, the effect of the position of PVX CP preceding the gene of interest was tested. It is evident from FIG. 4A that the location of CP after the triple gene block provides for a more efficient cell-to-cell movement than location of said CP between PVX RNA dependent RNA polymerase and the triple gene block. The provector system was also used in this experiment. No difference in the expression level of the protein of interest (GFP) was found between the cases where provectors or assembled vectors providing for PVX-derived RNA replicons were used (see Example 5, FIG. 5). When we included in comparative studies vectors that provide for RNA replicon containing CP after the gene of interest, the expression level (brightness of GFP expressing area) of said gene of interest from such vector was surprisingly significantly weaker compared with vectors where CP was positioned before the gene of interest (pICH20799 versus pICH25488 or pICH25491, FIG. 6, example 6).

In the examples, we use PVX-based RNA replicons. However, other viruses belonging to potexvirus taxonomic group can be used for the construction of RNA virus-based vectors according to the present invention. Viral species usable for the invention include but are not limited to bamboo mosaic potexvirus, papaya mosaic potexvirus, alternanthera mosaic potexvirus, clover yellow mosaic virus, plantain virus X, white clover mosaic virus and potato aucuba mosaic virus. For details on plant viral movement proteins, see the recent review of W J Lucas (2006, *Virology,* 344:169-184).

One RNA replicon derived from one plant virus may be used in the process of the invention, e.g. from potato virus X (PVX). However, two or more different RNA replicons may be used in a plant or plant tissue for expressing two different proteins of interest, whereby such different RNA replicons are preferably derived from different plant viruses. Such different plant viruses from which said different RNA replicons may be derived are preferably synergistic or non-competing viruses. "Synergistic" and "non-competing" are used herein synonymously. Synergistic viruses can coexist and efficiently amplify in the same plant cells. Similarly, RNA replicons derived from synergistic RNA viruses can co-exist and efficiently amplify in the same plant cells. An example of such a synergistic pair of RNA replicons is a pair of RNA replicons, whereby one RNA replicon is derived from TMV or TVCV and the other RNA replicon is derived from a potexvirus such as PVX. Synergistic RNA replicons may be used for the expression of two or more proteins or protein subunits of interest, such as the heavy and the light chain of a monoclonal antibody, in the same plant cell. Processes of expressing two or more proteins of interest in the same plant or in the same plant cells using different (non-competing) viral vectors is described in EP1686176.

In the examples, we predominantly used *Agrobacterium*-mediated delivery of viral vectors in plant cells. Various other methods usually used for stable transformation of plants may be used for the delivery of vectors into plant cells such as direct introduction of a heterologous nucleotide sequence into cells by means of microprojectile bombardment, electroporation or PEG-mediated transformation of protoplasts. *Agrobacterium*-mediated plant transformation is preferred. Thus, a heterologous nucleotide sequence may be transformed into plant cells by various technologies such as by a Ti-plasmid vector carried by *Agrobacterium* (U.S. Pat. No. 5,591,616; U.S. Pat. No. 4,940,838; U.S. Pat. No. 5,464,763), particle or microprojectile bombardment (U.S. Pat. No. 05,100,792; EP 00444882B1; EP 00434616B1). In principle, other plant transformation methods can also be used e.g. microinjection (WO 09209696; WO 09400583A1; EP 175966B1), electroporation (EP00564595B1; EP00290395B1; WO 08706614A1), etc. The choice of the transformation method depends inter alia on the plant species to be transformed. For example, microprojectile bombardment may be preferred for monocot transformation, while for dicots, *Agrobacterium*-mediated transformation gives generally better results.

The present invention is preferably carried out with higher, multi-cellular plants. Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to:

Representatives of *Graminae, Compositae, Solanacea* and *Rosaceae*. Additionally, preferred species for use in the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the *Olyreae*, the *Pharoideae* and many others.

In one specific embodiment of the process of the invention, RNA replicons derived from PVX are used with *Nicotiana* plants.

Proteins of interest, or fragments thereof, that can be expressed, in sense or antisense orientation, using the invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific. toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal -oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Ga14 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed using the system of the invention. Examples of such proteins of interest include inter alia the following proteins (pharmaceutical proteins): immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The content of European patent application No. 06 018 713.5, filed on Sep. 6, 2006, the priority of which is claimed by the present patent application is incorporated herein by reference in its entirety.

EXAMPLES

Example 1

PVX constructs lacking CP do not move from cell-to-cell

A PVX construct containing a GFP gene (pA3151) was obtained from Professor Yuri Dorokhov (Moscow State University, Russia). This construct was made by cloning a NheI-SalI fragment containing the GFP coding sequence into pPVX201 (Baulcombe, D., Chapman, S. & Santa Cruz, S., 1995, *Plant J.*, 7:1045-1053) digested with NheI and SalI, and then subcloning from the resulting construct a Hind3-SacI fragment (containing the entire viral insert and GFP gene) into pBIN19. The viral insert was then subcloned from pA3151 into pICBV52 (a small pBIN19-based Kan$^R$ binary vector) as a SacI-SphI fragment, resulting in plasmid pICH20799. This construct contains the PVX construct cloned under the control of the 35S promoter (FIG. 1B). The GFP coding sequence is expressed from a duplicated CP subgenomic promoter (sgc), and is located between the triple gene block (TGB) and the CP coding sequence. Since the duplicated subgenomic promoter fragment upstream of GFP also contained the CP start codon, the start codon was eliminated by mutation from ATG to AGG.

A control construct lacking CP was made from pICH20799 (FIG. 1B) by deleting the CP gene and its subgenomic promoter (using PCR with one of the primers overlapping the deletion endpoints). The resulting construct, pICH21333 (FIG. 1B), was transformed into *Agrobacterium* and infiltrated in a *Nicotiana benthamiana* leaf. As expected, viral replicons were unable to move from cell-to-cell or systemically. Movement of the replicons was rescued when pICH21333 was coinfiltrated together with constructs pICH10745 or pICH22066, which provide transient expression of TVCV MP or PVX CP, respectively (FIG. 1A). pICH10745 and pICH22066 constructs contain the TVCV MP or PVX CP coding sequences, respectively, under control of the 35S promoter.

Example 2

A PVX replicon with the TVCV MP gene cloned between the TGB and the gene of interest is able to move from cell to cell Since TVCV MP is able to provide cell-to-cell movement to PVX replicons that lack PVX CP, the TVCV MP gene was cloned in the PVX construct between the triple gene block and the gene of interest (GFP in this case), under control of a duplicated CP subgenomic promoter. For practical reasons, this construct (pICH22939, FIG. 2B and SEQ ID NO:1) was made as a 5' provector module which contains the 35S promoter fused to 5' viral vector sequences but lacks the 3' part of the construct including the coding sequence of the gene of interest and the PVX 3' NTR. A recombination site (the *Streptomyces* phage C31 AttP site) and intron sequences follow the viral construct sequences. A 3' provector module, pICH21282 FIG. 2B), contains a compatible recombination site (*Streptomyces* phage C31 AttB recombination site) followed by intron sequences, the GFP gene and the PVX NTR. The 5' and 3' parts of the construct are assembled in vivo by site-specific recombination at the recombination sites by coinfiltration of agrobacteria containing the 5' and 3' modules and the PhiC31 recombinase (pICH10881, containing the PhiC31 recombinase under control of the *Arabidopsis* ACT2 promoter, see Marillonnet et al., 2005, *Proc. Natl. Acad. Sci. USA,* 101: 6852-6857). After T-DNA delivery of the 5' and 3' modules to plant cells and recombination at the AttP and AttB sites, the recombined DNA is transcribed from the 35S promoter. The recombination site is excised from the transcript by splicing of the flanking intron sequences, and the spliced transcript exported from the nucleus to the cytoplasm where it is amplified as a normal viral RNA replicon.

Infiltration of a control provector construct (pICH22922, 5' provector without TVCV MP sequences) with the 3' provector pICH21282 led to the formation of replicons incapable of cell-to-cell movement. In contrast, infiltration of pICH22939 led to replicons that were capable to move from cell to cell (FIG. 2A).

Figure 2:
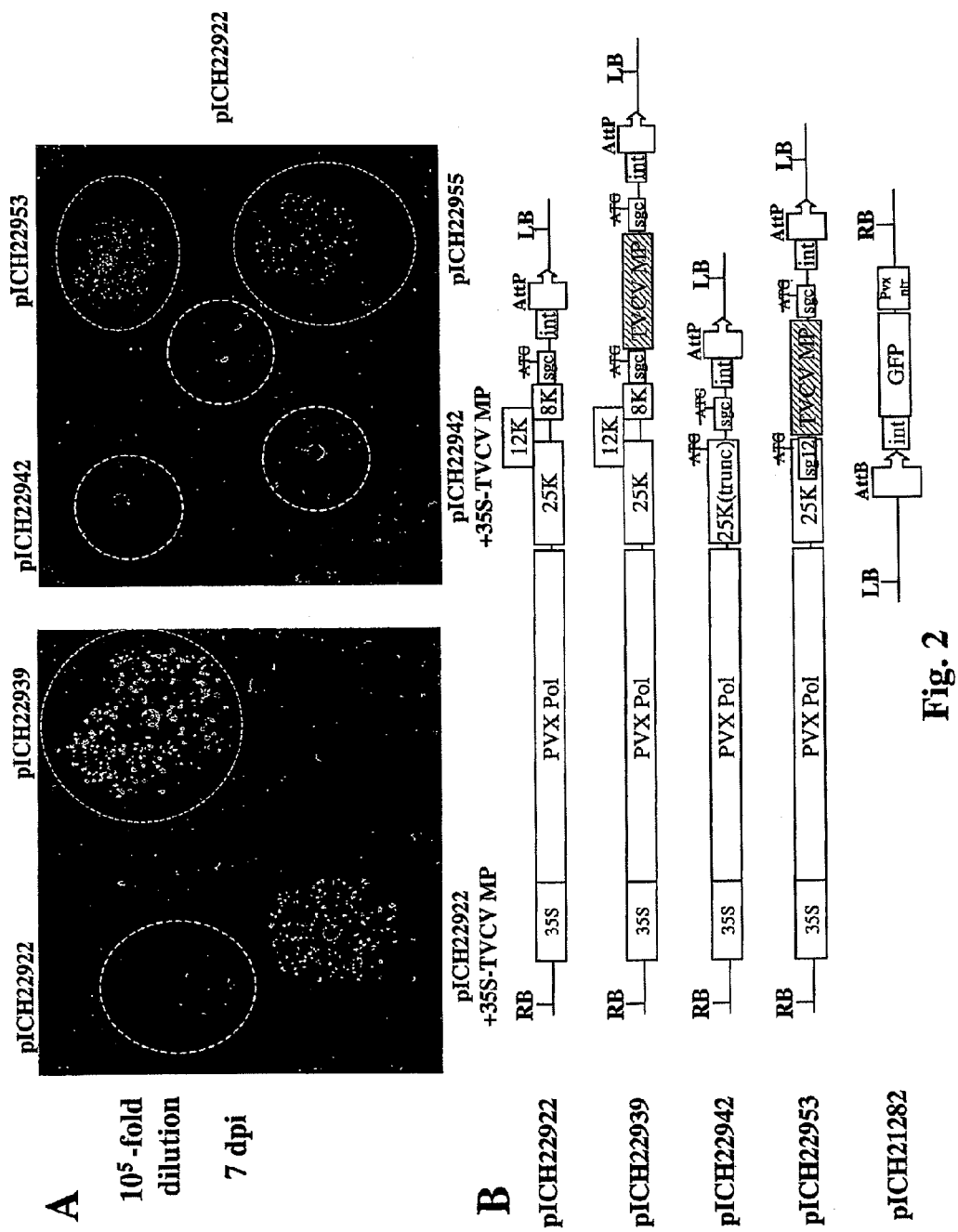
FIG. 2. Expression of GFP using different PVX provector modules. A—*N. benthamiana* leaves monitored under UV light after agro-infiltration with different 5' PVX provectors in combination with 3' provector pICH21282 and in the presence of phage C31 integrase providing for site-specific recombination-mediated assembly of viral replicon-encoding DNA. Only 5' provectors (e.g. pICH22922; pICH22942, etc.) mark the inoculation spots. 35S-TVCV MP: vector providing tobamovirus Turnip Vein Clearing Virus movement protein (MP) under control of the CaMV 35S promoter. The pictures were taken 7 days post infiltration (7 dpi). *Agrobacterium* suspensions used for infiltration were diluted $10^5$ fold for achieving an expression level allowing visual detection of differences in expression levels.

Since TMV is able to provide cell-to-cell movement to TMV replicons without the need for other viral proteins, a second PVX construct was made in which the 12K and 8K proteins of the triple-gene block were deleted, resulting in construct pICH22953 (FIG. 2B and SEQ ID NO:2). In this case, the TMV MP is expressed from the 12K subgenomic promoter (sg12). Infiltration of pICH22953 with pICH21282 led to replicons that were able to move from cell-to-cell. Cell-to-cell movement and GFP fluorescence were however not better or stronger than when using construct pICH22939 (FIG. 2).

Example 3

A PVX vector with a PVX CP gene cloned between the TGB and the gene of interest is able to move from cell to cell A construct similar to pICH22939 but with PVX CP replacing TVCV MP was made. The sequence of this construct is the same as that of the wild type virus from the 5' end of the virus up to the end of the CP. The CP is then followed by the duplicated CP subgenomic promoter that is used for expression of the gene of interest. Infiltration of this construct, pICH22988 (FIG. 3B), with pICH21282 (FIG. 2B) led to the formation of replicons that moved from cell to cell much faster and that produced brighter GFP fluorescence than replicons produced from pICH22939 (FIG. 3A).

Example 4

A PVX vector with a PVX CP gene cloned between the RdRP and the TGB is able to move cell-to-cell The PVX CP gene was cloned between the RdRp and the triple gene block, under control of a duplicated 25K subgenomic promoter (sg25), resulting in construct pICH24180 (FIG. 4B, SEQ ID NO:3). Infiltration of pICH24180 in combination with pICH21282 and an integrase source (pICH10881) led to the formation of viral replicons that were able to move from cell to cell (FIG. 4A). The construct pICH22577 (similar to pICH22922 but differ for a few restriction sites) was infiltrated instead of pICH24180 in control experiment and exhibited no cell-to-cell movement, as expected. As with pICH22988, GFP fluorescence from pICH24180 was stronger than with construct pICH22939.

Example 5

Complete assembled PVX viral vectors containing CP also provide cell-to-cell movement.

Assembled constructs including a 3' provector with GFP part (pICH21282, FIG. 2B) and corresponding to provectors pICH22988 or pICH24180 were made, yielding plasmids pICH25488 and pICH25491, respectively (FIG. 5B). The nucleotide sequences of the T-DNA region of pICH25488 and pICH25491 are given as SEQ ID NO:5 and SEQ ID NO:6, respectively. Both constructs were found to work like the provectors, as expected, and provided cell-to-cell movement and strong GFP fluorescence (FIG. 5A). GFP fluorescence was also much stronger than with the standard construct (pICH20799) in which the CP gene is located after the gene of interest suggesting expression of more recombinant protein (FIG. 6A). Coomassie-stained protein gels showed that a much higher amount of GFP protein was expressed from pICH25491 and pICH25488 than from pICH20799, and that in contrast, a much higher amount of PVX CP was produced from pICH20799 than from the other two constructs.

Example 6

PVX cloning vectors

A schematic representation of two types of PVX cloning vectors with CP between the RdRP and the TGB, or between the TGB and gene of interest, are shown in FIG. 7. CS: cloning sites.

SEQUENCE LISTING

<160> NUMBER OF SEQ ID NOS: 14

<210> SEQ ID NO 1
<211> LENGTH: 786
<212> TYPE: DNA
<213> ORGANISM: Artificial Sequence
<220> FEATURE:
<223> OTHER INFORMATION: Fragment of pICH22939 (subgenomic promoter-
      TMV MP, between 25K and subgenomic promoter-gene of interest)

<400> SEQUENCE: 1

```
tactcgaaag aggtcagcac cagctagaaa atgtcgatag tctcgtacga acctaaggtg      60
agtgatttcc tcaatctttc gaagaaggaa gagatcttgc cgaaggctct aacgaggtta     120
aaaaccgtgt ctattagtac taaagatatt atatctgtca aggagtcgga gactttgtgt     180
gatatagatt tgttaatcaa tgtgccatta gataagtata gatatgtggg tatcctagga     240
gctgttttta ccggagagtg gctagtgcca gacttcgtta aggtggagt gacgataagt      300 gtgatagata agcgtctggt gaactcaaag gagtgcgtga ttggtacgta cagagccgca     360
gccaagagta agaggttcca gttcaaattg gttccaaatt actttgtgtc caccgtggac     420
gcaaagagga agccgtggca ggttcatgtt cgtatacaag acttgaagat tgaggcgggt     480
tggcagccgt tagctctgga agtagtttca gttgctatgg tcaccaataa cgttgtcatg     540
aagggtttga gggaaaaggt cgtcgcaata atgatccgg acgtcgaagg tttcgaaggt      600
gtggttgacg aattcgtcga ttcggttgca gcatttaaag cggttgacaa tttcaggaag     660
aggaaaaaga aggttgaaga aagggatgta gtaagtaagt ataaatatag accggagaaa     720
tacgccggtc ctgattcgtt taatttaaaa gaagaaatg tcttacaaca ttacaaaccc      780
gaataa                                                                786
```

<210> SEQ ID NO 2
<211> LENGTH: 792
<212> TYPE: DNA
<213> ORGANISM: Artificial Sequence
<220> FEATURE:
<223> OTHER INFORMATION: Sequence fragment from pICH22953 containing the
      11 C-terminal aminoacids of the 25K coding sequence, followed by
      the TVCV MP coding sequence (the ATG of the 12K protein in the 25K
      sequence is mutated from ATG to ACG)

<400> SEQUENCE: 2

```
caaagggatt gacatacgtc cgcgcagggc catagaaaaa tgtcgatagt ctcgtacgaa      60
cctaaggtga gtgatttcct caatctttcg aagaaggaag agatcttgcc gaaggctcta    120
acgaggttaa aaaccgtgtc tattagtact aaagatatta tatctgtcaa ggagtcggag    180
actttgtgtg atatagattt gttaatcaat gtgccattag ataagtatag atatgtgggt    240
atcctaggag ctgtttttac cggagagtgg ctagtgccag acttcgttaa ggtggagtg     300 acgataagtg tgatagataa gcgtctggtg aactcaaagg agtgcgtgat tggtacgtac    360
agagccgcag ccaagagtaa gaggttccag ttcaaattgg ttccaaatta ctttgtgtcc    420
accgtggacg caaagaggaa gccgtggcag gttcatgttc gtatacaaga cttgaagatt    480
gaggcgggtt ggcagccgtt agctctggaa gtagtttcag ttgctatggt caccaataac    540
gttgtcatga agggtttgag ggaaaaggtc gtcgcaataa tgatccgga cgtcgaaggt      600 ttcgaaggtg tggttgacga attcgtcgat tcggttgcag catttaaagc ggttgacaat    660
ttcaggaaga ggaaaaagaa ggttgaagaa agggatgtag taagtaagta taaatataga    720
```

```
ccggagaaat acgccggtcc tgattcgttt aatttaaaag aagaaaatgt cttacaacat    780
tacaaacccg aa                                                        792

<210> SEQ ID NO 3
<211> LENGTH: 817
<212> TYPE: DNA
<213> ORGANISM: Artificial Sequence
<220> FEATURE:
<223> OTHER INFORMATION: Sequence fragment of pICH24180 including the 4
      last amino acids of the RdRP, the subgenomic promoter of the 25K
      gene, the PVX CP gene, the subgenomic promoter of the 25K gene and
      the first 4 aa of the 25K protein

<400> SEQUENCE: 3
agaaactttc tttaaccgtt aagttacctt agagatttga ataagatgtc agcaccagct     60
agcacaacac agcccatagg gtcaactacc tcaactacca caaaaactgc aggcgcaact    120
cctgccacag cttcaggcct gttcactatc ccggatgggg atttctttag tacagcccgt    180
gccatagtag ccagcaatgc tgtcgcaaca aatgaggacc tcagcaagat tgaggctatt    240
tggaaggaca tgaaggtgcc cacagacact atggcacagg ctgcttggga cttagtcaga    300
cactgtgctg atgtaggatc atccgctcaa acagaaatga tagatacagg tccctattcc    360
aacggcatca gcagagctag actggcagca gcaattaaag aggtgtgcac acttaggcaa    420
ttttgcatga agtatgcccc agtggtatgg aactggatgt taactaacaa cagtccacct    480
gctaactggc aagcacaagg tttcaagcct gagcacaaat tcgctgcatt cgacttcttc    540
aatggagtca ccaacccagc tgccatcatg cccaaagagg ggctcatccg gccaccgtct    600
gaagctgaaa tgaatgctgc ccaaactgct gcctttgtga agattacaaa ggccagggca    660
caatccaacg actttgccag cctagatgca gctgtcactc gaggtcgtat cactggaaca    720
acaaccgctg aggctgttgt cactctacca ccaccataac agaaactttc tttaaccgtt    780
aagttacctt agagatttga ataagatgga tattctc                             817

<210> SEQ ID NO 4
<211> LENGTH: 4371
<212> TYPE: DNA
<213> ORGANISM: Artificial Sequence
<220> FEATURE:
<223> OTHER INFORMATION: Sequence fragment of pICH25488 encoding RNA-
      dependent RNA polymerase

<400> SEQUENCE: 4
atggccaagg tgcgcgaggt ttaccaatct tttacagact ccaccacaaa aactctcatc     60
caagatgagg cttatagaaa cattcgcccc atcatggaaa acacaaaact agctaaccct    120
tacgctcaaa cggttgaagc ggctaatgat ctagaggggt tcggcatagc caccaatccc    180
tatagcattg aattgcatac acatgcagcc gctaagacca tagagaataa acttctagag    240
gtgcttggtt ccatcctacc acaagaacct gttacattta tgtttcttaa acccagaaag    300
ctaaactaca tgagaagaaa cccgcggatc aaggacattt ccaaaatgt tgccattgaa    360 ccaagagacg tagccaggta ccccaaggaa acaataattg acaaactcac agagatcaca    420
acggaaacag catacattag tgacactctg cacttcttgg atccgagcta catagtggag    480
acattccaaa actgcccaaa attgcaaaca ttgtatgcga ccttagttct ccccgttgag    540
gcagccttta aaatggaaag cactcacccg aacatataca gcctcaaata cttcggagat    600
ggtttccagt atatccagg caaccatggt ggcgggcat accatcatga attcgctcat    660
ctacaatggc tcaaagtggg aaagatcaag tggagggacc caaggatag ctttctcgga    720
```

```
catctcaatt acacgactga gcaggttgag atgcacacag tgacagtaca gttgcaggaa    780
tcgttcgcgg caaaccactt gtactgcatc aggagaggag acttgctcac accggaggtg    840
cgcactttcg gccaacctga caggtacgtg attccaccac agatcttcct cccaaaagtt    900
cacaactgca agaagccgat tctcaagaaa actatgatgc agctcttctt gtatgttagg    960
acagtcaagg tcgcaaaaaa ttgtgacatt tttgccaaag tcagacaatt aattaaatca   1020
tctgacttgg acaaatactc tgctgtggaa ctggtttact tagtaagcta catggagttc   1080
cttgccgatt tacaagctac cacctgcttc tcagacacac tttctggtgg cttgctaaca   1140
aagacccttg caccggtgag ggcttggata caagagaaaa agatgcagct gtttggtctt   1200
gaggactacg cgaagttagt caaagcagtt gatttccacc cggtggattt ttcttttcaaa  1260
gtggaaactt gggacttcag attccacccc ttgcaagcgt ggaaagcctt ccgaccaagg   1320
gaagtgtcgg atgtagagga aatggaaagt tgttctcag atggggacct gcttgattgc    1380
ttcacaagaa tgccagctta tgcggtaaac gcagaggaag atttagctgc aatcaggaaa   1440
acgcccgaga tggatgtcgg tcaagaagtt aaagagcctg caggagacag aaatcaatac   1500
tcaaaccctg cagaaacttt cctcaacaag ctccacagga aacacagtag ggaggtgaaa   1560
caccaggccg caaagaaagc taaacgccta gctgaaatcc aggagtcaat gagagctgaa   1620
ggtgatgccg aaccaaatga aataagcggg acgatggggg caatacccag caacgccgaa   1680
cttcctggca cgaatgatgc cagacaagaa ctcacactcc caaccactaa acctgtccct   1740
gcaaggtggg aagatgcttc attcacagat tctagtgtgg aagaggagca ggttaaactc   1800
cttggaaaag aaaccgttga acagcgacg caacaagtca tcgaaggact tccttggaaaa   1860
cactggattc ctcaattaaa tgctgttgga ttcaaggcgc tggaaattca gagggatagg   1920
agtggaacaa tgatcatgcc catcacagaa atggtgtccg ggctgaaaaa agaggacttc   1980
cctgaaggaa ctccaaaaga gttggcacga gaattgttcg ctatgaacag aagccctgcc   2040
accatccctt tggacctgct tagagccaga gactacggca gtgatgtaaa gaacaagaga   2100
attggtgcca tcacaaagac acaggcaacg agttggggcg aatacttgac aggaaagata   2160
gaaagcttaa ctgagaggaa agttgcgact tgtgtcattc atggagctgg aggttctgga   2220
aaaagtcatg ccatccagaa ggcattgaga gaaattggca agggctcgga catcactgta   2280
gtcctgccga ccaatgaact gcggctagat tggagtaaga agtgcctaa cactgagccc   2340
tatatgttca agacctctga aaaggcgtta attgggggaa caggcagcat agtcatcttt   2400
gacgattact caaaacttcc tcccggttac atagaagcct tagtctgttt ctactctaaa   2460
atcaagctaa tcattctaac aggagatagc agacaaagcg tctaccatga aactgctgag   2520
gacgcctcca tcaggcattt ggaccagca acagagtact tctcaaaata ctgccgatac   2580
tatctcaatg ccacacaccg caacaagaaa gatcttgcga acatgcttgg tgtctacagt   2640
gagagaacgg gagtcaccga atcagcatg agcgccgagt tcttagaagg aatcccaact   2700
ttggtaccct cggatgagaa gagaaagctg tacatgggca ccgggaggaa tgacacgttc   2760
acatacgctg gatgccaggg gctaactaag ccgaaggtac aaatagtgtt ggaccacaac   2820
acccaagtgt gtagcgcgaa tgtgatgtac acggcacttt ctagagccac cgataggatt   2880
cacttcgtga acacaagtgc aaattcctct gccttctggg aaaagttgga cagcacccct   2940
tacctcaaga ctttcctatc agtggtgaga gaacaagcac tcagggagta cgagccggca   3000
gaggcagagc caattcaaga gcctgagccc cagacacaca tgtgtgtcga aatgaggag   3060
tccgtgctag aagagtacaa agaggaactc ttggaaaagt ttgacagaga gatccactct   3120
```

```
gaatcccatg gtcattcaaa ctgtgtccaa actgaagaca caaccattca gttgttttcg   3180
catcaacaag caaaagatga gactctcctc tgggcgacta tagatgcgcg gctcaagacc   3240
agcaatcaag aaacaaactt ccgagaattc ctgagcaaga aggacattgg ggacgttctg   3300
tttttaaact accaaaaagc tatgggttta cccaaagagc gtattccttt ttcccaagag   3360
gtctgggaag cttgtgccca cgaagtacaa agcaagtacc tcagcaagtc aaagtgcaac   3420
ttgatcaatg ggactgtgag acagagccca gacttcgatg aaaataagat tatgtattc    3480 ctcaagtcgc agtgggtcac aaaggtggaa aaactaggtc tacccaagat taagccaggt   3540
caaaccatag cagccttta ccagcagact gtgatgcttt ttggaactat ggctaggtac    3600
atgcgatggt tcagacaggc tttccagcca aaagaagtct tcataaactg tgagacgacg   3660
ccagatgaca tgtctgcatg ggccttgaac aactggaatt tcagcagacc tagcttggct   3720
aatgactaca cagctttcga ccagtctcag gatggagcca tgttgcaatt tgaggtgctc   3780
aaagccaaac accactgcat accagaggaa atcattcagg catacataga tattaagact   3840
aatgcacaga ttttcctagg cacgttatca attatgcgcc tgactggtga aggtcccact   3900
tttgatgcaa acactgagtg caacatagct tacacccata caaagtttga catcccagcc   3960
ggaactgctc aagtttatgc aggagacgac tccgcactgg actgtgttcc agaagtgaag   4020 catagttttcc acaggcttga ggacaaatta ctcctaaagt caaagcctgt aatcacgcag   4080
caaaagaagg gcagttggcc tgagttttgt ggttggctga tcacaccaaa aggggtgatg   4140
aaagacccaa ttaagctcca tgttagctta aaattggctg aagctaaggg tgaactcaag   4200
aaatgtcaag attcctatga aattgatctg agttatgcct atgaccacaa ggactctctg   4260
catgacttgt tcgatgagaa acagtgtcag gcacacacac tcacttgcag aacactaatc   4320
aagtcaggga gaggcactgt ctcacttttcc cgcctcagaa actttctta a            4371

<210> SEQ ID NO 5
<211> LENGTH: 8070
<212> TYPE: DNA
<213> ORGANISM: Artificial Sequence
<220> FEATURE:
<223> OTHER INFORMATION: T-DNA region of plasmid pICH25488

<400> SEQUENCE: 5
cctgatctgg ggaaccctgt ggttggcaca tacaaatgga cgaacggata aaccttttca     60
cgccctttta aatatccgat tattctaata aacgctcttt tctcttaggt ttacccgcca    120
atatatcctg tcaaacactg atagtttaaa ctgaaggcgg gaaacgacaa tctgatctaa    180
gctaggcatg cctgcaggtc aacatggtgg agcacgacac gcttgtctac tccaaaaata    240
tcaaagatac agtctcagaa gaccaaaggg caattgagac ttttcaacaa agggtaatat    300
ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gacccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taaggaagtt    600
catttcattt ggagaggaga aaactaaacc atacaccacc aacacaacca aacccaccac    660
gcccaattgt tacacacccg cttgaaaaag aaagtttaac aaatggccaa ggtgcgcgag    720
gtttaccaat ctttttacaga ctccaccaca aaaactctca tccaagatga ggcttataga    780
aacattcgcc ccatcatgga aaaacacaaa ctagctaacc cttacgctca aacggttgaa    840
```

```
gcggctaatg atctagaggg gttcggcata gccaccaatc cctatagcat tgaattgcat    900
acacatgcag ccgctaagac catagagaat aaacttctag aggtgcttgg ttccatccta    960
ccacaagaac ctgttacatt tatgtttctt aaacccagaa agctaaacta catgagaaga   1020
aacccgcgga tcaaggacat tttccaaaat gttgccattg aaccaagaga cgtagccagg   1080
taccccaagg aaacaataat tgacaaactc acagagatca caacggaaac agcatacatt   1140
agtgacactc tgcacttctt ggatccgagc tacatagtgg agacattcca aaactgccca   1200
aaattgcaaa cattgtatgc gaccttagtt ctccccgttg aggcagcctt taaaatggaa   1260
agcactcacc cgaacatata cagcctcaaa tacttcggag atggtttcca gtatatacca   1320
ggcaaccatg gtggcggggc ataccatcat gaattcgctc atctacaatg gctcaaagtg   1380
ggaaagatca gtggaggga ccccaaggat agctttctcg acatctcaa ttacacgact    1440
gagcaggttg agatgcacac agtgacagta cagttgcagg aatcgttcgc ggcaaaccac   1500
ttgtactgca tcaggagagg agacttgctc acaccggagg tgcgcacttt cggccaacct   1560
gacaggtacg tgattccacc acagatcttc ctcccaaaag ttcacaactg caagaagccg   1620
attctcaaga aaactatgat gcagctcttc ttgtatgtta ggacagtcaa ggtcgcaaaa   1680
aattgtgaca ttttttgccaa agtcagacaa ttaattaaat catctgactt ggacaaatac   1740
tctgctgtgg aactggttta cttagtaagc tacatggagt tccttgccga tttacaagct   1800
accacctgct tctcagacac actttctggt ggcttgctaa caaagaccct tgcaccggtg   1860
agggcttgga tacaagagaa aaagatgcag ctgtttggtc ttgaggacta cgcgaagtta   1920
gtcaaagcag ttgatttcca cccggtggat ttttctttca aagtggaaac ttgggacttc   1980
agattccacc ccttgcaagc gtggaaagcc ttccgaccaa gggaagtgtc ggatgtagag   2040
gaaatggaaa gtttgttctc agatggggac ctgcttgatt gcttcacaag aatgccagct   2100
tatgcggtaa acgcagagga agatttagct gcaatcagga aaacgcccga gatggatgtc   2160
ggtcaagaag ttaaagagcc tgcaggagac agaaatcaat actcaaaccc tgcagaaact   2220
ttcctcaaca agctccacag gaaacacagt agggaggtga acaccaggc cgcaaagaaa   2280
gctaaacgcc tagctgaaat ccaggagtca atgagagctg aaggtgatgc cgaaccaaat   2340
gaaataagcg ggacgatggg ggcaataccc agcaacgccg aacttcctgg cacgaatgat   2400
gccagacaag aactcacact cccaaccact aaacctgtcc ctgcaaggtg ggaagatgct   2460
tcattcacag attctagtgt ggaagaggag caggttaaac tccttggaaa agaaaccgtt   2520
gaaacagcga cgcaacaagt catcgaagga cttccttgga acactggat tcctcaatta   2580
aatgctgttg gattcaaggc gctggaaatt cagagggata ggagtggaac aatgatcatg   2640
cccatcacag aaatggtgtc cgggctgaaa aagaggact tccctgaagg aactccaaaa   2700
gagttggcac gagaattgtt cgctatgaac agaagccctg ccaccatccc tttggacctg   2760
cttagagcca gagactacgg cagtgatgta agaacaagag aattggtgc catcacaaag   2820
acacaggcaa cgagttgggg cgaatacttg acaggaaaga tagaaagctt aactgagagg   2880
aaagttgcga cttgtgtcat tcatggagct ggaggttctg aaaaagtca tgccatccag   2940
aaggcattga gagaaattgg caagggctcg acatcactg tagtcctgcc gaccaatgaa   3000
ctgcggctag attggagtaa gaaagtgcct aacactgagc cctatatgtt caagacctct   3060
gaaaaggcgt taattgggg aacaggcagc atagtcatct ttgacgatta ctcaaaactt   3120
cctcccggtt acatagaagc cttagtctgt ttctactcta aaatcaagct aatcattcta   3180
acaggagata gcagacaaag cgtctaccat gaaactgctg aggacgcctc catcaggcat   3240
```

```
ttgggaccag caacagagta cttctcaaaa tactgccgat actatctcaa tgccacacac   3300
cgcaacaaga aagatcttgc gaacatgctt ggtgtctaca gtgagagaac gggagtcacc   3360
gaaatcagca tgagcgccga gttcttagaa ggaatcccaa ctttggtacc ctcggatgag   3420
aagagaaagc tgtacatggg caccggragg aatgacacgt tcacatacgc tggatgccag   3480
gggctaacta agccgaaggt acaaatagtg ttggaccaca acacccaagt gtgtagcgcg   3540
aatgtgatgt acacggcact ttctagagcc accgatagga ttcacttcgt gaacacaagt   3600
gcaaattcct ctgccttctg ggaaaagttg acagcaccc cttacctcaa gactttccta   3660
tcagtggtga gagaacaagc actcagggag tacgagccgg cagaggcaga gccaattcaa   3720
gagcctgagc cccagacaca catgtgtgtc gagaatgagg agtccgtgct agaagagtac   3780
aaagaggaac tcttggaaaa gtttgacaga gagatccact ctgaatccca tggtcattca   3840
aactgtgtcc aaactgaaga cacaaccatt cagttgtttt cgcatcaaca agcaaaagat   3900
gagactctcc tctgggcgac tatagatgcg cggctcaaga ccagcaatca agaaacaaac   3960
ttccgagaat tcctgagcaa gaaggacatt ggggacgttc tgtttttaaa ctaccaaaaa   4020
gctatgggtt tacccaaaga gcgtattcct ttttcccaag aggtctggga agcttgtgcc   4080
cacgaagtac aaagcaagta cctcagcaag tcaaagtgca acttgatcaa tgggactgtg   4140
agacagagcc cagacttcga tgaaaataag attatggtat tcctcaagtc gcagtgggtc   4200
acaaaggtgg aaaaactagg tctacccaag attaagccag gtcaaaccat agcagccttt   4260
taccagcaga ctgtgatgct ttttggaact atggctaggt acatgcgatg gttcagacag   4320
gctttccagc caaagaagt cttcataaac tgtgagacga cgccagatga catgtctgca   4380
tgggccttga caactggaa tttcagcaga cctagcttgg ctaatgacta cacagctttc   4440
gaccagtctc aggatggagc catgttgcaa tttgaggtgc tcaaagccaa acaccactgc   4500
ataccagagg aaatcattca ggcatacata gatattaaga ctaatgcaca gattttccta   4560
ggcacgttat caattatgcg cctgactggt gaaggtccca cttttgatgc aaacactgag   4620
tgcaacatag cttacaccca tacaaagttt gacatcccag ccggaactgc tcaagtttat   4680
gcaggagacg actccgcact ggactgtgtt ccagaagtga agcatagttt ccacaggctt   4740
gaggacaaat tactcctaaa gtcaaagcct gtaatcacgc agcaaaagaa gggcagttgg   4800
cctgagtttt gtggttggct gatcacacca aaagggggtga tgaaagaccc aattaagctc   4860
catgttagct taaaattggc tgaagctaag ggtgaactca gaaatgtca agattcctat   4920
gaaattgatc tgagttatgc ctatgaccac aaggactctc tgcatgactt gttcgatgag   4980
aaacagtgtc aggcacacac actcacttgc agaacactaa tcaagtcagg gagaggcact   5040
gtctcacttt cccgcctcag aaactttctt taaccgttaa gttaccttag agattttgaat   5100
aagatggata ttctcatcag tagtttgaaa agtttaggtt attctaggac ttccaaatct   5160
ttagattcag gacctttggt agtacatgca gtagccggag ccgtaagtc cacagcccta   5220
aggaagttga tcctcagaca cccaacattc accgtgcata cactcggtgt ccctgacaag   5280
gtgagtatca gaactagagg catacagaag ccaggaccta ttcctgaggg caacttcgca   5340
atcctcgatg agtatacttt ggacaacacc acaaggaact cataccaggc acttttgct   5400
gaccccttatc aggcaccgga gttcagccta gagcccact tctacttgga acatcatt t   5460
cgagttccga ggaaagtggc agatttgata gctggctgtg gcttcgattt cgagacgaac   5520
tcaccggaag aagggcactt agagatcact ggcatatca aagggccct actcggaaag   5580
gtgatagcca ttgatgagga gtctgagaca acactgtcca ggcatggtgt tgagtttgtt   5640
```

```
aagccctgcc aagtgacggg acttgagttc aaagtagtca ctattgtgtc tgccgcacca   5700
atagaggaaa ttggccagtc cacagctttc tacaacgcta tcaccaggtc aaagggattg   5760
acatatgtcc gcgcagggcc ataggctgac cgctccggtc aattctgaaa aagtgtacat   5820
agtattaggt ctatcatttg ctttagtttc aattaccttt ctgctttcta gaaatagctt   5880
accccacgtc ggtgacaaca ttcacagctt gccacacgga ggagcttaca gagacggcac   5940
caaagcaatc ttgtacaact ccccaaatct agggtcacga gtgagtctac acaacggaaa   6000
gaacgcagca tttgctgccg ttttgctact gactttgctg atctatggaa gtaaatacat   6060
atctcaacgc aatcatactt gtgcttgtgg taacaatcat agcagtcatt agcacttcct   6120
tagtgaggac tgaaccttgt gtcatcaaga ttactgggga atcaatcaca gtgttggctt   6180
gcaaactaga tgcagaaacc ataagggcca ttgccgatct caagccactc tccgttgaac   6240
ggttaagttt ccattgatac tcgaaagatg tcagcaccag ctagtacaac acagcccata   6300
gggtcaacta cctcaactac cacaaaaact gcaggcgcaa ctcctgccac agcttcaggc   6360
ctgttcacta tcccggatgg ggatttcttt agtacagccc gtgccatagt agccagcaat   6420
gctgtcgcaa caaatgagga cctcagcaag attgaggcta tttggaagga catgaaggtg   6480
cccacagaca ctatggcaca ggctgcttgg gacttagtca gacactgtgc tgatgtagga   6540
tcatccgctc aaacagaaat gatagataca ggtccctatt ccaacggcat cagcagagct   6600
agactggcag cagcaattaa agaggtgtgc acacttaggc aattttgcat gaagtatgcc   6660
ccagtggtat ggaactggat gttaactaac aacagtccac ctgctaactg gcaagcacaa   6720
ggtttcaagc ctgagcacaa attcgctgca ttcgacttct tcaatggagt caccaaccca   6780
gctgccatca tgcccaaaga ggggctcatc cggccaccgt ctgaagctga atgaatgct    6840
gcccaaactg ctgcctttgt gaagattaca aaggccaggg cacaatccaa cgactttgcc   6900
agcctagatg cagctgtcac tcgaggtcgt atcactggaa caacaaccgc tgaggctgtt   6960
gtcactctac caccaccata atgaacggtt aagtttccat tgatactcga aagaggtcag   7020
caccagctag caacaaacaa gaaatggtga gcaagggcga ggagctgttc accggggtgg   7080
tgcccatcct ggtcgagctg gacggcgacg taaacggcca caagttcagc gtgtccggcg   7140
agggcgaggg cgatgccacc tacggcaagc tgaccctgaa gttcatctgc accaccggca   7200
agctgcccgt gccctggccc acccttcgtga ccaccttcag ctacggcgtg cagtgcttca   7260
gccgctaccc cgaccacatg aagcagcacg acttcttcaa gtccgccatg cccgaaggct   7320
acgtccagga gcgcaccatc ttcttcaagg acgacggcaa ctacaagacc cgcgccgagg   7380
tgaagttcga gggcgacacc ctggtgaacc gcatcgagct gaagggcatc gacttcaagg   7440
aggacggcaa catcctgggg cacaagctgg agtacaacta caacagccac aacgtctata   7500
tcatggccga caagcagaag aacggcatca aggtgaactt caagatccgc cacaacatcg   7560
aggacggcag cgtgcagctc gccgaccact accagcagaa cacccccatc ggcgacggcc   7620
ccgtgctgct gcccgacaac cactacctga gcacccagtc cgccctgagc aaagacccca   7680
acgagaagcg cgatcacatg gtcctgctgg agttcgtgac cgccgccggg atcactcacg   7740
gcatggacga gctgtacaag taatctagcg ataccgtcga ctacgtctac ataaccgacg   7800
cctacccccag tttcatagta ttttctggtt tgattgtatg aataatataa ataaaaaaaa   7860
aaaaaaaaaa aaaaaactag tggtaccgag ctcttctgtc agcgggccca ctgcatccac   7920
cccagtacat taaaaacgtc cgcaatgtgt tattaagttg tctaagcgtc aatttgttta   7980
caccacaata tatcctgcca ccagccagcc aacagctccc cgaccggcag ctcggcacaa   8040
```

```
aatcaccact cgatacaggc agcccatcag                                    8070
```

<210> SEQ ID NO 6
<211> LENGTH: 8060
<212> TYPE: DNA
<213> ORGANISM: Artificial Sequence
<220> FEATURE:
<223> OTHER INFORMATION: T-DNA region of plasmid pICH25491

<400> SEQUENCE: 6

```
cctgtggttg gcacatacaa atggacgaac ggataaacct tttcacgccc ttttaaatat     60
ccgattattc taataaacgc tcttttctct taggtttacc cgccaatata tcctgtcaaa    120
cactgatagt ttaaactgaa ggcgggaaac gacaatctga tctaagctag gcatgcctgc    180
aggtcaacat ggtggagcac gacacgcttg tctactccaa aaatatcaaa gatacagtct    240
cagaagacca agggcaatt gagactttc aacaagggt aatatccgga aacctcctcg      300
gattccattg cccagctatc tgtcacttta ttgtgaagat agtggaaaag gaaggtggct    360
cctacaaatg ccatcattgc gataaaggaa aggccatcgt tgaagatgcc tctgccgaca    420
gtggtcccaa agatggaccc ccacccacga ggagcatcgt ggaaaaagaa gacgttccaa    480
ccacgtcttc aaagcaagtg gattgatgtg atatctccac tgacgtaagg gatgacgcac    540
aatcccacta tccttcgcaa gacccttcct ctatataagg aagttcattt catttggaga    600
ggagaaaact aaaccataca ccaccaacac aaccaaaccc accacgccca attgttacac    660
acccgcttga aaagaaagt ttaacaaatg gccaaggtgc gcgaggttta ccaatctttt    720
acagactcca ccacaaaaac tctcatccaa gatgaggctt atagaaacat tcgccccatc    780
atggaaaaac acaaactagc taaccccttac gctcaaacgg ttgaagcggc taatgatcta    840
gagggggttcg gcatagccac caatccctat agcattgaat tgcatacaca tgcagccgct    900
aagaccatag agaataaact tctagaggtg cttggttcca tcctaccaca gaacctgtt     960
acatttatgt ttcttaaacc cagaaagcta aactacatga aagaaaccc gcggatcaag   1020
gacatttttcc aaaatgttgc cattgaacca agagacgtag ccaggtaccc caaggaaaca   1080
ataattgaca aactcacaga gatcacaacg gaaacagcat acattagtga cactctgcac   1140
ttcttggatc cgagctacat agtggagaca ttccaaaact gcccaaaatt gcaaacattg   1200
tatgcgacct tagttctccc cgttgaggca gcctttaaaa tggaaagcac tcacccgaac   1260
atatacagcc tcaaatactt cggagatggt ttccagtata taccaggcaa ccatggtggc   1320
ggggcatacc atcatgaatt cgctcatcta caatggctca agtgggaaa gatcaagtgg   1380
agggaccca aggatagctt tctcggacat ctcaattaca cgactgagca ggttgagatg   1440
cacacagtga cagtacagtt gcaggaatcg ttcgcggcaa accacttgta ctgcatcagg   1500
agaggagact tgctcacacc ggaggtgcgc actttcggcc aacctgacag gtacgtgatt   1560
ccaccacaga tcttcctccc aaaagttcac aactgcaaga agccgattct caagaaaact   1620
atgatgcagc tcttcttgta tgttaggaca gtcaaggtcg caaaaaattg tgacattttt   1680
gccaaagtca gacaattaat taatcatct gacttgaca aatactctgc tgtgaactg     1740
gtttacttag taagctacat ggagttcctt gccgatttac aagctaccac ctgcttctca   1800
gacacactt ctggtggctt gctaacaaag acccttgcac cggtgagggc ttggatacaa   1860
gagaaaaga tgcagctgtt tggtcttgag gactacgcga agttagtcaa agcagttgat   1920
ttccacccgg tggattttttc tttcaaagtg gaaacttggg acttcagatt ccacccttg   1980
caagcgtgga aagccttccg accaagggaa gtgtcggatg tagaggaaat ggaaagtttg   2040
```

```
ttctcagatg gggacctgct tgattgcttc acaagaatgc cagcttatgc ggtaaacgca    2100
gaggaagatt tagctgcaat caggaaaacg cccgagatgg atgtcggtca agaagttaaa    2160
gagcctgcag gagacagaaa tcaatactca aaccctgcag aaactttcct caacaagctc    2220
cacaggaaac acagtaggga ggtgaaacac caggccgcaa agaaagctaa acgcctagct    2280
gaaatccagg agtcaatgag agctgaaggt gatgccgaac caaatgaaat aagcgggacg    2340 atggggggcaa tacccagcaa cgccgaactt cctggcacga atgatgccag acaagaactc    2400
acactcccaa ccactaaacc tgtccctgca aggtgggaag atgcttcatt cacagattct    2460
agtgtggaag aggagcaggt taaactcctt ggaaaagaaa ccgttgaaac agcgacgcaa    2520
caagtcatcg aaggacttcc ttggaaacac tggattcctc aattaaatgc tgttggattc    2580
aaggcgctgg aaattcagag ggataggagt ggaacaatga tcatgcccat cacagaaatg    2640
gtgtccgggc tggaaaaaga ggacttccct gaaggaactc caaaagagtt ggcacgagaa    2700
ttgttcgcta tgaacagaag ccctgccacc atccctttgg acctgcttag agccagagac    2760
tacggcagtg atgtaaagaa caagagaatt ggtgccatca caaagacaca ggcaacgagt    2820
tggggcgaat acttgacagg aaagatagaa agcttaactg agaggaaagt tgcgacttgt    2880
gtcattcatg gagctggagg ttctggaaaa agtcatgcca tccagaaggc attgagagaa    2940
attggcaagg gctcggacat cactgtagtc ctgccgacca tgaactgcg gctagattgg    3000 agtaagaaag tgcctaacac tgagccctat atgttcaaga cctctgaaaa ggcgttaatt    3060
gggggaacag gcagcatagt catctttgac gattactcaa aacttcctcc cggttacata    3120
gaagccttag tctgtttcta ctctaaaatc aagctaatca ttctaacagg agatagcaga    3180
caaagcgtct accatgaaac tgctgaggac gcctccatca ggcatttggg accagcaaca    3240
gagtacttct caaaatactg ccgatactat ctcaatgcca cacaccgcaa caagaaagat    3300
cttgcgaaca tgcttggtgt ctacagtgag agaacgggag tcaccgaaat cagcatgagc    3360
gccgagttct tagaaggaat cccaactttg gtaccctcgg atgagaagag aaagctgtac    3420
atgggcaccg ggaggaatga cacgttcaca tacgctggat gccagggggct aactaagccg    3480 aaggtacaaa tagtgttgga ccacaacacc caagtgtgta gcgcgaatgt gatgtacacg    3540
gcactttcta gagccaccga taggattcac ttcgtgaaca caagtgcaaa ttcctctgcc    3600
ttctgggaaa agttggacag cacccctttac ctcaagactt tcctatcagt ggtgagagaa    3660
caagcactca gggagtacga gccggcagag gcagagccaa ttcaagagcc tgagccccag    3720
acacacatgt gtgtcgagaa tgaggagtcc gtgctagaag agtacaaaga ggaactcttg    3780
gaaaagtttg acagagagat ccactctgaa tcccatggtc attcaaactg tgtccaaact    3840
gaagacacaa ccattcagtt gttttcgcat caacaagcaa aagatgagac tctcctctgg    3900
gcgactatag atgcgcggct caagaccagc aatcaagaaa caaacttccg agaattcctg    3960
agcaagaagg acattgggga cgttctgttt ttaaactacc aaaaagctat gggtttaccc    4020
aaagagcgta ttcctttttc ccaagaggtc tgggaagctt gtgcccacga agtacaaagc    4080
aagtacctca gcaagtcaaa gtgcaacttg atcaatggga ctgtgagaca gagcccagac    4140
ttcgatgaaa ataagattat ggtattcctc aagtcgcagt gggtcacaaa ggtggaaaaa    4200
ctaggtctac ccaagattaa gccaggtcaa accatagcag ccttttacca gcagactgtg    4260 atgcttttg gaactatggc taggtacatg cgatggttca acaggctttt ccagccaaaa    4320
gaagtcttca taaactgtga gacgacgcca gatgacatgt ctgcatgggc cttgaacaac    4380
tggaatttca gcagacctag cttggctaat gactacacag ctttcgacca gtctcaggat    4440
```

```
ggagccatgt tgcaatttga ggtgctcaaa gccaaacacc actgcatacc agaggaaatc    4500
attcaggcat acatagatat taagactaat gcacagattt tcctaggcac gttatcaatt    4560
atgcgcctga ctggtgaagg tcccacttt gatgcaaaca ctgagtgcaa catagcttac    4620
acccatacaa agtttgacat cccagccgga actgctcaag tttatgcagg agacgactcc    4680
gcactggact gtgttccaga agtgaagcat agtttccaca ggcttgagga caaattactc    4740
ctaaagtcaa agcctgtaat cacgcagcaa agaagggca gttggcctga gttttgtggt    4800
tggctgatca caccaaaagg ggtgatgaaa gacccaatta agctccatgt tagcttaaaa    4860
ttggctgaag ctaagggtga actcaagaaa tgtcaagatt cctatgaaat tgatctgagt    4920
tatgcctatg accacaagga ctctctgcat gacttgttcg atgagaaaca gtgtcaggca    4980
cacacactca cttgcagaac actaatcaag tcagggagag gcactgtctc actttcccgc    5040
ctcagaaact ttcttaacc gttaagttac cttagagatt tgaataagat gtcagcacca    5100
gctagcacaa cacagcccat agggtcaact acctcaacta ccacaaaaac tgcaggcgca    5160
actcctgcca cagcttcagg cctgttcact atcccggatg gggatttctt tagtacagcc    5220
cgtgccatag tagccagcaa tgctgtcgca acaaatgagg acctcagcaa gattgaggct    5280
atttggaagg acatgaaggt gcccacagac actatggcac aggctgcttg ggacttagtc    5340
agacactgtg ctgatgtagg atcatccgct caaacagaaa tgatagatac aggtccctat    5400
tccaacggca tcagcagagc tagactggca gcagcaatta agaggtgtg cacacttagg    5460 caattttgca tgaagtatgc cccagtggta tggaactgga tgttaactaa caacagtcca    5520
cctgctaact ggcaagcaca aggtttcaag cctgagcaca aattcgctgc attcgacttc    5580
ttcaatggag tcaccaaccc agctgccatc atgcccaaag agggctcat ccggccaccg    5640 tctgaagctg aaatgaatgc tgcccaaact gctgcctttg tgaagattac aaaggccagg    5700
gcacaatcca acgactttgc cagcctagat gcagctgtca ctcgaggtcg tatcactgga    5760
acaacaaccg ctgaggctgt tgtcactcta ccaccaccat aacagaaact ttctttaacc    5820
gttaagttac cttagagatt tgaataagat ggatattctc atcagtagtt tgaaaagttt    5880
aggttattct aggacttcca aatctttaga ttcaggacct ttggtagtac atgcagtagc    5940
cggagccggt aagtccacag ccctaaggaa gttgatcctc agacacccaa cattcaccgt    6000
gcatacactc ggtgtccctg acaaggtgag tatcagaact agaggcatac agaagccagg    6060
acctattcct gagggcaact tcgcaatcct cgatgagtat actttggaca acaccacaag    6120
gaactcatac caggcacttt ttgctgaccc ttatcaggca ccggagttta gcctagagcc    6180
ccacttctac ttggaaacat catttcgagt tccgaggaaa gtggcagatt tgatagctgg    6240
ctgtggcttc gatttcgaga cgaactcacc ggaagaaggg cacttagaga tcactggcat    6300
attcaaaggg cccctactcg gaaaggtgat agccattgat gaggagtctg agacaacact    6360
gtccaggcat ggtgttgagt ttgttaagcc ctgccaagtg acgggacttg agttcaaagt    6420
agtcactatt gtgtctgccg caccaataga ggaaattggc cagtccacag ctttctacaa    6480
cgctatcacc aggtcaaagg gattgacata tgtccgcgca gggccatagg ctgaccgctc    6540
cggtcaattc tgaaaaagtg tacatagtat taggtctatc atttgcttta gtttcaatta    6600
cctttctgct ttctagaaat agcttacccc acgtcggtga caacattcac agcttgccac    6660
acggaggagc ttacagagac ggcaccaaag caatcttgta caactcccca aatctagggt    6720
cacgagtgag tctacacaac ggaaagaacg cagcatttgc tgccgttttg ctactgactt    6780
tgctgatcta tggaagtaaa tacatatctc aacgcaatca tacttgtgct tgtggtaaca    6840
```

-continued

| | |
|---|---|
| atcatagcag tcattagcac ttccttagtg aggactgaac cttgtgtcat caagattact | 6900 |
| ggggaatcaa tcacagtgtt ggcttgcaaa ctagatgcag aaaccataag ggccattgcc | 6960 |
| gatctcaagc cactctccgt tgaacggtta agtttccatt gatactcgaa agaggtcagc | 7020 |
| accagctagc aacaaacaag aaatggtgag caagggcgag gagctgttca ccggggtggt | 7080 |
| gcccatcctg gtcgagctgg acggcgacgt aaacggccac aagttcagcg tgtccggcga | 7140 |
| gggcgagggc gatgccacct acggcaagct gaccctgaag ttcatctgca ccaccggcaa | 7200 |
| gctgcccgtg ccctggccca cccctcgtgac caccttcagc tacggcgtgc agtgcttcag | 7260 |
| ccgctacccc gaccacatga agcagcacga cttcttcaag tccgccatgc ccgaaggcta | 7320 |
| cgtccaggag cgcaccatct tcttcaagga cgacggcaac tacaagaccc gcgccgaggt | 7380 |
| gaagttcgag ggcgacaccc tggtgaaccg catcgagctg aagggcatcg acttcaagga | 7440 |
| ggacggcaac atcctggggc acaagctgga gtacaactac aacagccaca acgtctatat | 7500 |
| catggccgac aagcagaaga acggcatcaa ggtgaacttc aagatccgcc acaacatcga | 7560 |
| ggacggcagc gtgcagctcg ccgaccacta ccagcagaac ccccatcg cgacggccc | 7620 |
| cgtgctgctg cccgacaacc actacctgag cacccagtcc gccctgagca agacccccaa | 7680 |
| cgagaagcgc gatcacatgg tcctgctgga gttcgtgacc gccgccggga tcactcacgg | 7740 |
| catggacgag ctgtacaagt aatctagcga taccgtcgac tacgtctaca taaccgacgc | 7800 |
| ctaccccagt ttcatagtat tttctggttt gattgtatga ataatataaa taaaaaaaaa | 7860 |
| aaaaaaaaaa aaaaactagt ggtaccgagc tcttctgtca gcgggcccac tgcatccacc | 7920 |
| ccagtacatt aaaaacgtcc gcaatgtgtt attaagttgt ctaagcgtca atttgtttac | 7980 |
| accacaatat atcctgccac cagccagcca acagctcccc gaccggcagc tcggcacaaa | 8040 |
| atcaccactc gatacaggca | 8060 |

<210> SEQ ID NO 7
<211> LENGTH: 714
<212> TYPE: DNA
<213> ORGANISM: Potato virus X

<400> SEQUENCE: 7

| | |
|---|---|
| atgtcagcac cagctagcac aacacagccc atagggtcaa ctacctcaac taccacaaaa | 60 |
| actgcaggcg caactcctgc cacagcttca ggcctgttca ctatcccgga tggggatttc | 120 |
| tttagtacag cccgtgccat agtagccagc aatgctgtcg caacaaatga ggacctcagc | 180 |
| aagattgagg ctatttggaa ggacatgaag gtgcccacag acactatggc acaggctgct | 240 |
| tgggacttag tcagacactg tgctgatgta ggatcatccg ctcaaacaga aatgatagat | 300 |
| acaggtccct attccaacgg catcagcaga gctagactgg cagcagcaat taagaggtg | 360 |
| tgcacactta ggcaattttg catgaagtat gccccagtgg tatggaactg atgttaact | 420 |
| aacaacagtc cacctgctaa ctggcaagca caaggtttca agcctgagca caaattcgct | 480 |
| gcattcgact tcttcaatgg agtcaccaac ccagctgcca tcatgcccaa agagggctc | 540 |
| atccggccac cgtctgaagc tgaaatgaat gctgcccaaa ctgctgcctt tgtgaagatt | 600 |
| acaaaggcca gggcacaatc caacgacttt gccagcctag atgcagctgt cactcgaggt | 660 |
| cgtatcactg gaacaacaac cgctgaggct gttgtcactc taccaccacc ataa | 714 |

<210> SEQ ID NO 8
<211> LENGTH: 237
<212> TYPE: PRT
<213> ORGANISM: Potato virus X

<400> SEQUENCE: 8

```
Met Ser Ala Pro Ala Ser Thr Thr Gln Pro Ile Gly Ser Thr Thr Ser
1               5                   10                  15

Thr Thr Thr Lys Thr Ala Gly Ala Thr Pro Ala Thr Ala Ser Gly Leu
            20                  25                  30

Phe Thr Ile Pro Asp Gly Asp Phe Phe Ser Thr Ala Arg Ala Ile Val
        35                  40                  45

Ala Ser Asn Ala Val Ala Thr Asn Glu Asp Leu Ser Lys Ile Glu Ala
    50                  55                  60

Ile Trp Lys Asp Met Lys Val Pro Thr Asp Thr Met Ala Gln Ala Ala
65                  70                  75                  80

Trp Asp Leu Val Arg His Cys Ala Asp Val Gly Ser Ser Ala Gln Thr
                85                  90                  95

Glu Met Ile Asp Thr Gly Pro Tyr Ser Asn Gly Ile Ser Arg Ala Arg
            100                 105                 110

Leu Ala Ala Ala Ile Lys Glu Val Cys Thr Leu Arg Gln Phe Cys Met
            115                 120                 125

Lys Tyr Ala Pro Val Val Trp Asn Trp Met Leu Thr Asn Asn Ser Pro
130                 135                 140

Pro Ala Asn Trp Gln Ala Gln Gly Phe Lys Pro Glu His Lys Phe Ala
145                 150                 155                 160

Ala Phe Asp Phe Phe Asn Gly Val Thr Asn Pro Ala Ala Ile Met Pro
                165                 170                 175

Lys Glu Gly Leu Ile Arg Pro Pro Ser Glu Ala Glu Met Asn Ala Ala
            180                 185                 190

Gln Thr Ala Ala Phe Val Lys Ile Thr Lys Ala Arg Ala Gln Ser Asn
        195                 200                 205

Asp Phe Ala Ser Leu Asp Ala Ala Val Thr Arg Gly Arg Ile Thr Gly
    210                 215                 220

Thr Thr Thr Ala Glu Ala Val Val Thr Leu Pro Pro Pro
225                 230                 235
```

<210> SEQ ID NO 9
<211> LENGTH: 681
<212> TYPE: DNA
<213> ORGANISM: Potato virus X

<400> SEQUENCE: 9

```
atggatattc tcatcagtag tttgaaaagt ttaggttatt ctaggacttc caaatcttta      60
gattcaggac ctttggtagt acatgcagta gccggagccg taagtccaca gccctaagg     120
aagttgatcc tcagacaccc aacattcacc gtgcatacac tcggtgtccc tgacaaggtg    180
agtatcagaa ctagaggcat acagaagcca ggacctattc tgagggcaa cttcgcaatc     240
ctcgatgagt atactttgga caacaccaca aggaactcat accaggcact ttttgctgac    300
ccttatcagg caccggagtt tagcctagag ccccacttct acttggaaac atcatttcga    360
gttccgagga agtggcaga tttgatagct ggctgtggct tcgatttcga cgaactca      420
ccggaagaag ggcacttaga gatcactggc atattcaaag gccccctact cggaaaggtg    480
atagccattg atgaggagtc tgagacaaca ctgtccaggc atggtgttga gtttgttaag    540
ccctgccaag tgacgggact tgagttcaaa gtagtcacta ttgtgtctgc cgcaccaata    600
gaggaaattg ccagtccac agctttctac aacgctatca ccaggtcaaa gggattgaca    660
tatgtccgcg cagggccata g                                              681
```

```
<210> SEQ ID NO 10
<211> LENGTH: 226
<212> TYPE: PRT
<213> ORGANISM: Potato virus X

<400> SEQUENCE: 10

Met Asp Ile Leu Ile Ser Ser Leu Lys Ser Leu Gly Tyr Ser Arg Thr
1               5                   10                  15

Ser Lys Ser Leu Asp Ser Gly Pro Leu Val Val His Ala Val Ala Gly
            20                  25                  30

Ala Gly Lys Ser Thr Ala Leu Arg Lys Leu Ile Leu Arg His Pro Thr
        35                  40                  45

Phe Thr Val His Thr Leu Gly Val Pro Asp Lys Val Ser Ile Arg Thr
    50                  55                  60

Arg Gly Ile Gln Lys Pro Gly Pro Ile Pro Glu Gly Asn Phe Ala Ile
65                  70                  75                  80

Leu Asp Glu Tyr Thr Leu Asp Asn Thr Thr Arg Asn Ser Tyr Gln Ala
                85                  90                  95

Leu Phe Ala Asp Pro Tyr Gln Ala Pro Glu Phe Ser Leu Glu Pro His
            100                 105                 110

Phe Tyr Leu Glu Thr Ser Phe Arg Val Pro Arg Lys Val Ala Asp Leu
        115                 120                 125

Ile Ala Gly Cys Gly Phe Asp Phe Glu Thr Asn Ser Pro Glu Glu Gly
    130                 135                 140

His Leu Glu Ile Thr Gly Ile Phe Lys Gly Pro Leu Leu Gly Lys Val
145                 150                 155                 160

Ile Ala Ile Asp Glu Glu Ser Glu Thr Thr Leu Ser Arg His Gly Val
                165                 170                 175

Glu Phe Val Lys Pro Cys Gln Val Thr Gly Leu Glu Phe Lys Val Val
            180                 185                 190

Thr Ile Val Ser Ala Ala Pro Ile Glu Glu Ile Gly Gln Ser Thr Ala
        195                 200                 205

Phe Tyr Asn Ala Ile Thr Arg Ser Lys Gly Leu Thr Tyr Val Arg Ala
    210                 215                 220

Gly Pro
225

<210> SEQ ID NO 11
<211> LENGTH: 345
<212> TYPE: DNA
<213> ORGANISM: Potato virus X

<400> SEQUENCE: 11
atgtccgcgc agggccatag gctgaccgct ccggtcaatt ctgaaaaagt gtacatagta    60
ttaggtctat catttgcttt agtttcaatt acctttctgc tttctagaaa tagcttaccc   120
cacgtcggtg acaacattca cagcttgcca cacggaggag cttacagaga cggcaccaaa   180
gcaatcttgt acaactcccc aaatctaggg tcacgagtga gtctacacaa cggaaagaac   240
gcagcatttg ctgccgtttt gctactgact ttgctgatct atggaagtaa atacatatct   300
caacgcaatc atacttgtgc ttgtggtaac aatcatagca gtcat              345

<210> SEQ ID NO 12
<211> LENGTH: 115
<212> TYPE: PRT
<213> ORGANISM: Potato virus X

<400> SEQUENCE: 12
```

```
Met Ser Ala Gln Gly His Arg Leu Thr Ala Pro Val Asn Ser Glu Lys
1               5                   10                  15

Val Tyr Ile Val Leu Gly Leu Ser Phe Ala Leu Val Ser Ile Thr Phe
                20                  25                  30

Leu Leu Ser Arg Asn Ser Leu Pro His Val Gly Asp Asn Ile His Ser
            35                  40                  45

Leu Pro His Gly Gly Ala Tyr Arg Asp Gly Thr Lys Ala Ile Leu Tyr
        50                  55                  60

Asn Ser Pro Asn Leu Gly Ser Arg Val Ser Leu His Asn Gly Lys Asn
65                  70                  75                  80

Ala Ala Phe Ala Ala Val Leu Leu Leu Thr Leu Leu Ile Tyr Gly Ser
                85                  90                  95

Lys Tyr Ile Ser Gln Arg Asn His Thr Cys Ala Cys Gly Asn Asn His
                100                 105                 110

Ser Ser His
        115

<210> SEQ ID NO 13
<211> LENGTH: 210
<212> TYPE: DNA
<213> ORGANISM: Potato virus X

<400> SEQUENCE: 13
atggaagtaa atacatatct caacgcaatc atacttgtgc ttgtggtaac aatcatagca      60
gtcattagca cttccttagt gaggactgaa ccttgtgtca tcaagattac tggggaatca    120
atcacagtgt tggcttgcaa actagatgca gaaaccataa gggccattgc cgatctcaag    180
ccactctccg ttgaacggtt aagtttccat                                      210

<210> SEQ ID NO 14
<211> LENGTH: 70
<212> TYPE: PRT
<213> ORGANISM: Potato virus X

<400> SEQUENCE: 14

Met Glu Val Asn Thr Tyr Leu Asn Ala Ile Ile Leu Val Leu Val Val
1               5                   10                  15

Thr Ile Ile Ala Val Ile Ser Thr Ser Leu Val Arg Thr Glu Pro Cys
                20                  25                  30

Val Ile Lys Ile Thr Gly Glu Ser Ile Thr Val Leu Ala Cys Lys Leu
            35                  40                  45

Asp Ala Glu Thr Ile Arg Ala Ile Ala Asp Leu Lys Pro Leu Ser Val
        50                  55                  60

Glu Arg Leu Ser Phe His
65                  70
```

The invention claimed is:

1. Nucleic acid comprising or encoding an RNA replicon comprising, in this order, the following segments (i) to (iii):
   (i) a nucleic acid sequence encoding a potexvirus RNA-dependent RNA polymerase;
   (ii) a nucleic acid sequence comprising:
      (a) a potexvirus triple gene block and
      (b) a sequence encoding a potexviral coat protein;
      wherein items (a) and (b) can be in any order in said nucleic acid sequence of item (ii) and
   (iii) a heterologous nucleic acid sequence comprising a coding sequence of a protein of interest and a sub-genomic promoter for expressing said protein of interest from said replicon in a plant or in plant tissue;
   wherein said potexvirus triple gene block encodes three proteins as follows: a first protein comprising the protein sequence of SEQ ID NO: 10; a second protein comprising the protein sequence of SEQ ID NO: 12; and a third protein comprising the protein sequence of SEQ ID NO: 14, wherein said potexviral coat protein comprises a protein sequence of SEQ ID NO: 8, and wherein said sequence of item (i) encodes a protein having a sequence identical to a protein encoded by SEQ ID NO:4.

2. The nucleic acid according to claim 1, said nucleic acid further comprising a sequence selected from the group consisting of a transcription promoter active in plant cells upstream of item (i), a viral subgenomic promoter, and a potexviral 5' or 3' untranslated region.

3. The nucleic acid according to claim 1, wherein, in item (ii), said potexvirus triple gene block is located upstream of said potexviral coat protein gene.

4. A nucleic acid comprising a complementary sequence of a nucleic acid comprising or encoding an RNA replicon comprising, in this order, the following segments (i) to (iii):
  (i) a nucleic acid sequence encoding a potexvirus RNA-dependent RNA polymerase;
  (ii) a nucleic acid sequence comprising:
    (a) a potexvirus triple gene block and
    (b) a sequence encoding a potexviral coat protein;
    wherein items (a) and (b) can be in any order in said nucleic acid sequence of item (ii) and
  (iii) a heterologous nucleic acid sequence comprising a coding sequence of a protein of interest and a sub-genomic promoter for expressing said protein of interest from said replicon in a plant or in plant tissue;
wherein said potexvirus triple gene block encodes three proteins as follows: a first protein comprising the protein sequence of SEQ ID NO: 10; a second protein comprising the protein sequence of SEQ ID NO: 12; and a third protein comprising the protein sequence of SEQ ID NO: 14, wherein said potexviral coat protein comprises a protein sequence of SEQ ID NO: 8, and wherein said sequence of item (i) encodes a protein having a sequence identical to a protein encoded by SEQ ID NO:4.

5. A process of expressing a heterologous nucleic acid sequence of interest in a plant or in plant tissue, comprising providing a plant or plant tissue with a nucleic acid comprising or encoding an RNA replicon comprising, in this order, the following segments (i) to (iii):
  (i) a nucleic acid sequence encoding a potexvirus RNA-dependent RNA polymerase;
  (ii) a nucleic acid sequence comprising:
    (a) a potexvirus triple gene block and
    (b) a sequence encoding a potexviral coat protein;
    wherein items (a) and (b) can be in any order in said nucleic acid sequence of item (ii) and
  (iii) a heterologous nucleic acid sequence comprising a coding sequence of a protein of interest and a sub-genomic promoter for expressing said protein of interest from said replicon in a plant or in plant tissue;
wherein said potexvirus triple gene block encodes three proteins as follows: a first protein comprising the protein sequence of SEQ ID NO: 10; a second protein comprising the protein sequence of SEQ ID NO: 12; and a third protein comprising the protein sequence of SEQ ID NO: 14, wherein said potexviral coat protein comprises a protein sequence of SEQ ID NO: 8, and wherein said sequence of item (i) encodes a protein having a sequence identical to a protein encoded by SEQ ID NO:4.

* * * * *

UNITED STATES PATENT AND TRADEMARK OFFICE
CERTIFICATE OF CORRECTION

PATENT NO. : 8,415,463 B2  
APPLICATION NO. : 12/438743  
DATED : April 9, 2013  
INVENTOR(S) : Marillonnet et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

IN THE SPECIFICATION
Column 1, line 7, delete "PCT/EP2007/00785" and insert - -PCT/EP2007/007785- - therefor.
Column 1, line 9, delete "of" and insert - -in- - therefor.
Column 1, line 11, delete "Sep. 3, 2006" and insert - -Sep. 6, 2006- - therefor.
Column 1, line 29, delete "at" and insert - -et- - therefor.
Column 1, line 37, delete "at" and insert - -et- - therefor.
Column 1, line 49, delete "at" and insert - -et- - therefor.
Column 1, line 49, delete "at" and insert - -et- - therefor.
Column 2, line 3, delete "*Lend*" and insert - -*Lond*- - therefor.
Column 5, line 38, delete "PVXBK" and insert - -PVX8K- - therefor.
Column 10, lines 4 and 5, delete "pICH-122939" and insert - -pICH22939- - therefor.
Column 13, line 62, after "specific" delete the period ".".
Column 14, line 26, delete "Ga1 4" and insert –Gal4– therefor.

Signed and Sealed this  
Seventeenth Day of September, 2013

Teresa Stanek Rea  
*Deputy Director of the United States Patent and Trademark Office*